US006660513B2

(12) United States Patent
Mengeling et al.

(10) Patent No.: US 6,660,513 B2
(45) Date of Patent: Dec. 9, 2003

(54) PORCINE REPRODUCTIVE AND RESPIRATORY SYNDROME VACCINE, BASED ON ISOLATE JA-142

(75) Inventors: William L. Mengeling, Ames, IA (US); Ann Vorwald, Ames, IA (US); Kelly Lager, Neveda, IA (US); Mike Roof, Ames, IA (US); Kelly Burkhart, Radcliffe, IA (US); David E. Gorcyca, St. Joseph, MO (US)

(73) Assignees: USDA, Peoria, IL (US); Boehringer Ingelheim Corp., Ridgefield, CT (US)

( * ) Notice: Subject to any disclaimer, the term of this patent is extended or adjusted under 35 U.S.C. 154(b) by 0 days.

(21) Appl. No.: 10/143,186

(22) Filed: May 9, 2002

(65) Prior Publication Data

US 2003/0072771 A1 Apr. 17, 2003

Related U.S. Application Data

(63) Continuation of application No. 09/461,879, filed on Dec. 15, 1999, which is a continuation-in-part of application No. 09/298,110, filed on Apr. 22, 1999, now abandoned.

(51) Int. Cl.$^7$ .............................. C12N 7/00; C12Q 1/68
(52) U.S. Cl. .................... 435/235.1; 435/325; 435/239; 435/6
(58) Field of Search .................... 435/6, 235.1, 325, 435/239; 424/204.1, 184.1, 218.1, 209.1

(56) References Cited

U.S. PATENT DOCUMENTS

| | | | |
|---|---|---|---|
| 4,554,159 A | | 11/1985 | Roizman et al. |
| 5,476,778 A | * | 12/1995 | Chladek et al. ......... 435/235.1 |
| 5,510,258 A | | 4/1996 | Sanderson et al. |
| 5,587,164 A | | 12/1996 | Sanderson et al. |
| 5,698,203 A | | 12/1997 | Visser et al. |
| 5,840,563 A | | 11/1998 | Chladek et al. |
| 5,846,805 A | | 12/1998 | Collins et al. |
| 5,925,359 A | * | 7/1999 | Van Woensel et al. ... 424/204.1 |
| 6,042,830 A | * | 3/2000 | Chladek et al. ......... 424/184.1 |

FOREIGN PATENT DOCUMENTS

| | | |
|---|---|---|
| EP | 595436 | 5/1994 |
| EP | 0676467 | 11/1995 |
| WO | WO 93/03760 * | 3/1993 |
| WO | WO 94/18311 * | 8/1994 |

OTHER PUBLICATIONS

Andreyev, et al.; Genetic variation and phylogenetic relationships of 22 porcine reproductive and respiratory syndrome virus (PRRSV) field strains based on sequence analysis of open reading frame 5; Arch Virol (1997) 142: 993–1001.
Flint et al; Virus Cultivation, Detection, and Genetics; Arch Virol (2000) Chapter 2 40–42.
Nuttall; Growth Characteristics of Two Strains of Bovine Virus Diarrhoea Virus; Arch Virol (1980) 66 365–369.
Gong et al.; Characterization of RNA Synthesis during a one–step growth curve and of the replication mechanism of bovine viral diarrhoea virus; Journal of General Virology (1996) 77 2729–2736.
Horsfall et al.; General Principles of Animal Virus Multiplication; Viral and Rickettsial Infections of Man (1965) 239–241.
Wesley et al.; Differentiation of Vaccine (Strain Resp-PRRS®) and Field Strains of Porcine Reproductive and Respiratory Syndorme Virus by Restriction Enzyme Analysis; American Association of Swine Practitioners (1996) 141–143.
For purification of viral RNA from Plasma, Serum, Cell–free body fluids, Cell–culture supernatants; QIAamp® Viral RNA Mini Kit Handbook; QIAGEN (1999) Cat # 52906 1–35.
ENZO Biochem Inc. v Gen–Probe Incorporated et al; No. 01–01230; Decided Jul. 15, 2002.

* cited by examiner

Primary Examiner—Ali R. Salimi
(74) Attorney, Agent, or Firm—Hovey Williams LLP

(57) ABSTRACT

Substantially avirulent forms of atypical porcine reproductive and respiratory syndrome (PRRS) virus and corresponding vaccines are provided which result from cell culture passaging of virulent forms of PRRS. The resultant avirulent atypical PRRS virus is useful as a vaccine in that PRRS specific antibody response is elicited by inoculation of host animals, thereby conferring effective immunity against both previously known strains of PRRS virus and newly isolated atypical PRRS virus strains. The preferred passaging technique ensures that the virus remains in a logarithmic growth phase substantially throughout the process, which minimizes the time required to achieve attenuation.

10 Claims, No Drawings

SEQUENCE LISTING

<160> NUMBER OF SEQ ID NOS: 2

<210> SEQ ID NO 1
<211> LENGTH: 15424
<212> TYPE: DNA
<213> ORGANISM: Porcine reproductive and respiratory syndrome virus

<400> SEQUENCE: 1

| | | | | | |
|---|---|---|---|---|---|
| tcgcccgggc | aggtgttggc | tctatgcctt | ggcatttgta | ttgtcaggag | ctgcgaccat | 60 |
| tggcacagcc | caaaactagc | tgcacagaaa | acgcccttct | gtgacagccc | tcttcagggg | 120 |
| agcttagggg | tctgtcccta | gcaccttgct | tccggagttg | cactgcttta | cggtctctcc | 180 |
| aaccctttaa | ccatgtctgg | gatacttgat | cggtgcacgt | gcacccccaa | tgccagggtg | 240 |
| tttatggcgg | agggccaagt | ctactgcaca | cgatgtctca | gtgcacggtc | tctccttcct | 300 |
| ctgaatctcc | aagttcctga | gcttggagtg | ctgggcctat | tttacaggcc | cgaagagcca | 360 |

-continued

```
ctccggtggaa cgttgccacg tgcattcccc actgttgagt gctccccgc cggggcctgc     420 tggctttctg cgatctttcc aattgcacga atgaccagtg gaaacctgaa ctttcaacaa     480
agaatggtgc gggtcgcagc tgagatttac agagccggcc agctcacccc tgcagtcttg     540
aaggctctac aagtttatga acggggttgc cgctggtacc ctatagtcgg acctgtccct     600
ggagtggccg attttgccaa ctccctacat gtgagtgata aacctttccc gggagcaact     660
catgtgctaa ccaacctgcc actcccagag aggcctaagc ctgaagactt ttgcccttct     720
gagtgtgcta tggctgacgt ctatgatatt ggccatggcg ccgtcatgta tgtggccaaa     780
gggaaagtct cctgggcccc tcgtggcggg gatgaggcga aatttgaacc tgtccctagg     840
gagttgaagt tgatcgcgaa ccaactccac atctccttcc cgccccacca cgcagtggac     900
atgtctaagt ttgtgttcat agccctgggg agtggtgtct ctatgcgggt cgagtgccca     960
cacggctgtc tccccgctaa tactgtccct gaaggtaact gctggtggcg cttgtttgac    1020
tcgctcccac tggacgttca gaacaaagaa attgccgtg ccaaccaatt cggctatcaa    1080
accaagcatg tgtcgctgg caagtaccta caacggaggc tgcaagctaa tggtctccga    1140
gcagtgactg atacagatgg acccattgtc gtacagtatt tctctgttag ggagagctgg    1200
atccgccact tcagactggc ggaagagcct agcctccctg ggtttgaaga cctcctcaga    1260
ataagggtag agcccaatac gtcgccattg agtgacaagg gtggaaaaat cttccggttt    1320
ggcagtcaca aatggtacgg tgctggaaag agagcaagga aagcacgctc tggtatgacc    1380
accacagtcg ctcaccgcgc cttgcccgct cgtgaaatcc agcaagccaa aaagcacgag    1440
gatgccggcg ctgataaggc tgtgcatctc aggcactatt ctccgcctgc cgacgggaac    1500
tgtggttggc actgcatttc cgccatcgcc aaccgaatgg tgaattccaa atttgaaact    1560
actcttcccg agagggtgag accttcagat gactgggcta ctgacgagga ccttgtgaac    1620
accatccaaa ttctcaagct ccctgcggcc ttggacagga acggtgcttg tgttggcgcc    1680
aaatacgtgc ttaagctgga aggcgagcat tggactgtct ctgtgaccct tgggatgtcc    1740
ccttctttgc tccccttgta atgtgttcag ggctgttgtg agcataagag cggacttggt    1800
cccccagatg cggtcgaagt tttcggattt gaccctgcct gccttgaccg actggctgag    1860
gtaatgcact tgcctagcag tgtcatccca gctgctctgg ccgaaatgtc cggcgaccc     1920 aaccgtccgg cttccccggt cactactgtg tggactgttt cacaattctt tgcccgccac    1980
agaggaggag agcaccctga tcaggtgcgc ttaggaaaaa tcatcagcct ttgtcaagtt    2040
gttgaggaat gctgttgcca tcagaataaa accaaccggg ccaccccgga agaggttgcg    2100
gcaaggattg atcagtacct ccatggtgca acaagtcttg aagaatgctt gattaggctt    2160
gagagggttt gcccgccgag cgctgcggac accttctttg attggaatgt tgtgctccct    2220
ggggttgggg cttcaactca gacaaccaaa cagctccatg tcaaccagtg ccgcgctctg    2280
gttcctgtcg tgactcaaga gccttggac aaagacccag tccctctgac cgccttctcg    2340
ctgtccaatt gctactatcc tgcacaaggt gacgaggttc gtcaccgtga gggctaaac     2400 tccgtactct ctaagctgga gggggttgtt cgtgaggaat atgggctcac gccaactgga    2460
cctggcccgc gacccgcact accgaacggg ctcgtcgaac ttaaagacca gatggaggag    2520
gatctgctaa aactagtcaa cgcccaggca acttcagaaa tgatggcctg gcagccgag     2580 caggttgatc tgaaagcttg ggtcaaaaac taccacggt ggacaccgtc accccctcca    2640
ccaagagttc agcctcgaaa aacaaagcct gtcaagagct tgccagggaa caaacctgtc    2700
```

-continued

```
cccgctccac gcaggaaggt cagatctgat tgtggcagcc cgatttcgat gggcgacaat    2760
gttcctgacg gtcgggaaga tttgactgtt ggtggccccc ttgatctttc gacaccatcc    2820
gagccgatga cacctctgag tgagcctgca cctatgcccg cgttgcaata tatttctagg    2880
ccagtgacac ctttgagtgt gctggcccca gtacctgcac cgcgtagaac tgtgtcccga    2940
ccggtgacgc ccttgagtga gccaattttt tgtgtctgca cgcgacacaa atttcagcag    3000
gtggaagaag cgaatctggc ggcaacaatg ctgacgcacc aggacgaacc tctagatttg    3060
tctgcatcct cacagactga atatgaggct ctcccctaa caccactgca gaacatgggt    3120
attctggagg tggggggggca agaagctgag gaagttctga gtgaaaactc ggatacactg    3180
aatgacatca accctgcacc tgtgtcatca agcagctccc tgtcaagtgt taagatcaca    3240
cgcccaaaac actctgctca agccatcatt gactcgggcg ggccctgcag tgggcatctc    3300
cgaaagggaa aagaagcatg cctcagcatc atgcgtgagg cttgtgatgc ggctaagctt    3360
agtgaccctg ccacgcagga atggctttct cgcatgtggg ataggttga tatgctgact    3420
tggcgcaaca cgtctgctta ccaggcgttc cgcatcttag atggtaggtt tgagtttctc    3480
ccaaagatga tactcgagac accgccgccc tacccgtgtg ggtttgtgat gctgcctcgc    3540
acgcctgcac cttccgtggg tgcagagagt gaccttacca ttggttcagt cgccactgaa    3600
gatgttccac gcatcctcgg gaaaatagaa aacgccggca agatgcccaa ccaggggctc    3660
ttgacatcct tcggggaaga accggtgtgc gaccaacctg tcaaggactc ctggatgtcg    3720
tcgcgggggt ttgacgagag cacaacggct ccgtccgctg gtacaggtgg tgctgactta    3780
cccaccgatt tgccaccttc agatggtttg gatgcggacg agtgggggcc gttacggacg    3840
gtaagaaaga aagctgaaag gctcttcgac caattgagcc gtcaggtttt taacctcgtc    3900
tcccatctcc ctgttttctt ctcacacctc ttcaaatctg acagtggtta ttctccgggt    3960
gattgggggtt ttgcagcttt tactttattt tgcctctttt tgtgttacag ctacccattc    4020
tttggttttg ttcccctctt gggtgttttt tctgggtctt ctcggcgtgt gcgcatgggg    4080
gttttttggct gttggttggc ttttgctgtt ggcctgttca agcctgtgtc cgacccagtc    4140
ggcactgctt gtgagtttga ctcgccagag tgtaggaacg tccttcattc ttttgagctt    4200
ctcaaacctt gggaccctgt tcgcagcctt gttgtgggcc ccgtcggtct cggccttgcc    4260
attcttggca ggttactggg cggggcacgc tacatctggc attttttgct taggcttggc    4320
attgttgcag attgtatctt ggctggagct tatgtgcttt tcaaggtag gtgtaaaaag    4380
tgctggggat cttgtgtaag aactgctcct aatgaaatcg ccttcaacgt gttccctttt    4440
acgcgtgcga ccaggtcgtc actcatcgac ctgtgcgatc ggttttgtgc gccaaaaggc    4500
atggacccca ttttcctcgc tactgggtgg cgcgggtgct ggaacggccg aagtcccatt    4560
gagcaacccct ctgaaaaacc catcgcgttc gcccagttgg atgaaaagag gatcacggct    4620
agaactgtgg tcgctcagcc ttatgatcct aaccaagccg taaagtgctt gcgggtgtta    4680
caggcgggtg gggcgatagt ggccgaggca gtcccaaaag tggtcaaggt ttccgctatt    4740
ccattccgag ctccctttttt tcccaccgga gtgaaggttg atcctgagtg caggatcgtg    4800
gtcgaccccg acacttttac tacagctctc cggtctggtt actccaccac aaacctcgtc    4860
cttggtgtag gggactttgc ccaactgaat ggattaaaaa tcaggcaaat ttccaagccc    4920
tcgggaggag gccgcacct cattgctgcc ctgcatgttg cttgctcgat ggcgttgcac    4980
atgcttgctg gagtttatgt aactgcagtg gggtcttgcg gtaccggcac caacgatccg    5040
tggtgcacta acccattcgc cgtccctggc tacggacctg ctccctctg cacgtccaga    5100
```

```
ttgtgcatct cccaacatgg ccttaccctg cccttgacag cacttgtggc aggattcggt    5160
cttcaggaaa ttgccctagt cgttttgatt ttcgtttcca tcggaggcat ggctcatagg    5220
ttgagttgta aggctgatat gctgtgcgtc ttacttgcaa tcgccagcta tgtttgggta    5280 cccttacct ggttgctctg tgtgtttcct tgctggttgc gctggttctc tttgcaccct    5340
ctcaccattc tatggttggt gttttcttg atgtctgtaa atatgccttc gggaatctta    5400
accgtggtgt tattggttgc tctttggctt ctaggccgtt atactaatgt tgttggtctt    5460 gttacccct atgatattca ccattacacc aatggcccc cgtgttgc cgccttggct    5520 accgcaccag atgggactta cttggccgct gtccgccgcg ctgcgttgac tggccgcacc    5580
gtgctgttta ccccgtctca gcttgggtcc cttcttgagg gcgctttcag aactcgaaag    5640
ccctcactga acaccgtcaa tgtggtcggg tcctccatgg gctctggcgg agtgttcact    5700
atcgatggga aaattaagtg cgtgactgcc gcacatgtcc ttacgggtaa ttcagccagg    5760
gtttccgggg tcggctttaa tcaaatgctt gactttgatg taaaggggga cttcgccata    5820
gctgactgcc cgaattggca aggggctgct cctaagaccc aattctgcga ggatggatgg    5880
actggccgcg cctattggct gacatcctct ggcgtcgaac ccggtgtcat tgggaatgga    5940
ttcgccttct gcttcaccgc gtgcggcgat tccgggtccc cagtgatcac cgaagccggt    6000
gagcttgtcg gcgttcacac aggatcaaac aaacaaggag gaggcattgt tacgcgcccc    6060
tctggccagt tttgcaatgt ggcacccatc aagctgagcg aattaagtga gttctttgct    6120
ggacctaagg tcccgctcgg tgatgtgaag gttggcagcc ataattaa agacatatgc    6180 gaggtaccttcagatctttg cgccttgctt gctgccaaac ccgaactgga aggaggcctc    6240
tccaccgtcc aacttctgtg tgtgtttttc ctcctgtgga gatgatggg acatgcctgg    6300 acgcccttgg ttgctgttgg gttttttatc ttgaatgagg ttctcccagc tgtactggtc    6360
cggagtgttt tctcctttgg aatgtttgtg ctatcttggc tcacaccatg gtctgcgcaa    6420
gttctgatga tcaggcttct aacagcagct cttaacagga acagattgtc actcgccttt    6480
tacagccttg gtgcagcgac cggttttgtc gcagatctgg cggcaactca agggcacccg    6540
ttgcaggcag taatgaattt aagtacctat gccttcctgc ctcggataat ggtcgtgacc    6600
tcaccagtcc cagtgattgc gtgtggtgtt gtgcacctcc ttgccataat tttgtacttg    6660
tttaagtacc gctgcctgca caatgtcctt gttggcgatg gtgcgttctc tgcggctttc    6720
ttcttgcgat acttttgccga ggggaaattg agggaagggg tgtcgcaatc ctgcgggatg    6780
aatcatgagt cgctgactgg tgccctcgct atgagactta atgacgagga cttggatttt    6840
cttacgaaat ggactgattt taagtgtttt gtttctgcat ccaacatgag gaatgcggcg    6900
ggccagttca tcgaggctgc ctatgctaaa gcacttagaa ttgaacttgc ccagttggtg    6960
caggttgata aggttcgagg tactttggcc aaacttgaag cttttgctga taccgtggca    7020
ccccaactct cgcccggtga cattgttgtt gctcttggcc atacgcctgt ggcggtatc    7080 ttcgacctaa aggttggtag caccaagcat accctccaag ccattgagac cagagttctt    7140
gccgggtcca aaatgaccgt ggcgcgtgtc gttgatccaa ccccacacc cccacccgca    7200 cccgtgccta tccccttcc accgaaagtt ctggagaatg tccccaacgc tgggggggat    7260
gaggatcgtt tgaataagaa gaagaggcgc aagatggaag ccgtcggcat ctttgttatg    7320 ggtgaaaga aatatcagaa attttgggac aagaactccg tgatgtgtt ttatgaggag    7380 gtccatgata acacagacgc gtgggagtgc ctcagagttg acaaccctgc cgactttgac    7440
```

-continued

```
cctgagaagg gaactctgtg cgggcatact accattgaag ataagactta cagtgtctac    7500
gcctccccat ctggcaagaa attcctggtc cccgcctacc cagagagcaa aaaaaaccaa    7560
tgggaagctg cgaagctttc cgtggaacag gcccttggca tgatgaatgt cgacggtgaa    7620
ctgacagcca aagaagtgga gaaactgaaa agaataattg acaaactcca gggcctgact    7680
aaggagcagt gtttaaactg ctagccgcca gcggcttgac ccgctgtggt cgcggcggct    7740
tggttattac tgagacagcg gtaaaaatag tcaaatttca caaccggacc ttcaccctag    7800
gacctgtgaa tttaaaagtg gccagtgagg ttgagctaaa agacgcggtc gagcataacc    7860
aacacccggt tgcaagaccg gttgatggtg gtgttgtgct cctgcgctcc gcagttcctt    7920
cgcttataga cgtcttaatc tccggcgctg atgcatctcc caagttactc gcccgccacg    7980
ggccgggaaa cactgggatc gatggcacgc tttgggattt tgaggccgag gccactaaag    8040
aggaaattgc actcagtgcg caaataatac aggcttgtga cattaggcgc ggcgacgcac    8100
ctgaaattgg tcttccttat aagctgtacc ctgtcagggg caaccctgag cgggtaaaag    8160
gagtttttaca gaatacaagg tttgagagata taccttataa acccccagt gacactggaa    8220
gcccagtgca cgcggctgcc tgcctcacgc ccaatgccac tccggtgact gatgggcgct    8280
ccgtcttggc cacgactatg ccctccggtt ttgagttgta tgtaccgacc attccagcgt    8340
ctgtccttga ttatcttgat tctaggcctg actgccccaa acagttgaca gagcacggct    8400
gtgaggacgc cgcattaaga gacctctcca agtatgactt gtccacccaa ggctttgttt    8460
tacctggagt tcttcgcctt gtgcgtaagt acctgtttgc tcatgtgggt aagtgcccgc    8520
ccgttcatcg gccttccact taccctgcca agaattctat ggctggaata aatgggaaca    8580
ggtttccaac caaggacatc cagagcgtcc ctgaaatcga cgttctgtgc gcacaggccg    8640
ttcgggaaaa ctggcaaact gttacccctt gtaccctcaa gaaacagtat tgtgggaaga    8700
agaagactag gacaatactc ggcaccaata acttcattgc gctggctcac cgggcagcgt    8760
tgagtggtgt cacccagggc ttcatgaaaa aggcgtttaa ctcgcccatt gccctcggta    8820
aaaacaaatt taaagagctt cagactccgg tcttaggcag gtgccttgaa gctgatcttg    8880
catcctgcga tcgctccaca cctgcaattg tccgctggtt tgccgccaat cttctttatg    8940
aacttgcctg tgctgaagag caccagccgt cgtacgtgtt gaactgctgc cacgacctac    9000
tggtcacgca gtccggcgca gtaactaaga gaggtggcct gtcgtctggc gacccgatca    9060
cttctgtgtc caacaccatt tacagcttgg tgatatatgc acaacacatg gtgctcagtt    9120
actttaaaag tggtcaccct catggccttc tgtttctaca agaccagctg aagtttgagg    9180
acatgctcaa ggttcaaccc ctgatcgtct attcggacga cctcgtactg tatgccgagt    9240
ctcccaccat gccaaactac cactggtggg ttgaacatct gaacctgatg ctgggttttc    9300
agacggaccc aaagaagaca gccataacag actcgccatc atttctaggc tgtaggataa    9360
taaatggacg ccagctcgtc cctaaccgtg acaggattct cgcggccctc gcctaccata    9420
tgaaggcaag caatgtctct gaatactacg cctcggcggc tgcgatactc atggacagct    9480
gtgcttgttt agagtatgat cccgaatggt ttgaagagct tgtagttggg atagcgcagt    9540
gtgcccgcaa ggacggctac agttttcccg gcccgccgtt cttcttgtcc atgtgggaaa    9600
aactcagatc caatcatgag gggaagaagt ccagaatgtg cgggtactgc ggggcccgg    9660
ctccgtacgc cactgcctgt ggcctcgacg tctgtattta ccacacccac ttccaccagc    9720
attgtccagt catcatctgg tgtggccacc cggctggttc tggttcttgt agtgagtgca    9780
aaccccccct agggaaaggc acaagccctc tagatgaggt gttagaacaa gtcccgtata    9840
```

-continued

```
agcctccacg gactgtaatc atgcatgtgg agcagggtct caccctctt gacccaggca    9900
gataccagac tcgccgcgga ttagtctccg ttaggcgtgg cattagagga aatgaggttg    9960
atctaccaga cggtgattat gctagcaccg ccctactccc tacttgtaaa gagattaaca   10020
tggtcgctgt cgcctctaat gtgttgcgca gcaggttcat catcggcccg cctggtgctg   10080
ggaaaacata ctggctcctt caacaggtcc aggatggtga tgccatttac acgccaactc   10140
accagaccat gctcgatatg attagggctt tggggacgtg ccggttcaac gtcccagcag   10200
gtacgacgct gcaattccct gccccctccc gtaccggccc ttgggttcgc atcctagccg   10260
gcggttggtg tcctggcaag aattccttcc tggatgaagc agcgtattgt aatcaccttg   10320
atgtcttgag gcttcttagc aaaactaccc tcacctgtct gggagatttc aaacaactcc   10380
acccagtggg ttttgattct cattgctatg tttttgacat catgcctcag actcaactga   10440
agaccatctg gagatttgga cagaatatct gtgaggccat tcagccagat tacagggaca   10500
aacttgtatc catggtcaac acaacccgtg taacctacgt ggaaaaacct gtcaagtatg   10560
ggcaagtcct cacccttac cacagggacc gagaggacgg cgccatcaca attgactcca   10620
gtcaaggcgc acatttgat gtggttacac tgcatttgcc cactaaagat tcactcaaca   10680
ggcaaagagc ccttgttgct attaccaggg caagacatgc tgtctttgtg tatgacccac   10740
acaggcaact gcagagcatg tttgatcttc ctgcgaaagg cacaccgtc aacctcgctg   10800
tgcaccgtga cgagcagctg atcgtgctag atagaaataa caagaatgc acggttgctc   10860
aggctctagg caatggggat aaattcaggg ccacagacaa gcgcgttgta gattctctcc   10920
gcgccatttg tgcagatctg aagggtcga gctccccgct cccaaggtc gcacacaact   10980
tgggatttta tttctcgcct gatttgacac agtttgctaa actcccggta gaacttgcac   11040
cccactggcc cgtggtgaca acccagaaca atgaaaagtg gccagaccgg ttggttgcta   11100
gccttcgccc cgtccataag tatagccgcg cgtgcatcgg tgccggctac atggtgggcc   11160
cctcagtgtt tctgggcacc cctggggttg tgtcatacta tctcacaaaa tttgtcaggg   11220
gcgaggctca aatgcttccg gagacagtct tcagcaccgg ccgaattgag gtagattgcc   11280
gtgagtatct cgatgaccgg gagcgagaaa ttgctgagtc cctcccccat gctttcattg   11340
gcgacgtcaa aggcactacc gttggaggat gtcaccatgt cacctccaaa taccttccgc   11400
gcttccttcc caaggaatca gtcgcggtag tcggggtttc aagccccggg aaagccgcaa   11460
aagcagtttg cacattaaca gatgtgtatc tcccagatct cgaagcttac ctccacccag   11520
agacccagtc caagtgctgg aaaatgatgt tggacttcaa ggaagttcga ctgatggtct   11580
ggaaggacaa gacggcctat tttcaacttg aaggccgcca tttcacctgg taccagcttg   11640
caagctatgc ctcgtacatc cgagttcctg ttaactctac ggtgtatttg gacccctgca   11700
tgggccctgc cctttgcaac agaagagttg tcgggtccac tcattgggga gctgacctcg   11760
cagtcacccc ttatgattac ggtgccaaaa tcatcctgtc tagtgcatac catggtgaaa   11820
tgccccctgg gtacaaaatc ctggcgtgcg cggagttctc gcttgacgat ccagtgaggt   11880
acaaacacac ctgggggttt gaatcggata cagcgtatct gtacgagttc accggaaacg   11940
gtgaggactg ggaggattac aatgatgcgt ttcgtgcgcg ccagaaaggg aaaatttata   12000
aggccactgc caccagcatg aggtttcatt ttccccggg ccctgtcatt gaaccaactt   12060
taggcctgaa ttgaaatgaa atggggtcca tgcaaagcct ctttgacaaa attggccaac   12120
ttttcgtgga tgctttcacg gaattttggg tgtccattgt tgatatcatc atattttggg   12180
```

```
ccattttgtt tggctttacc atcgctggct ggctggtggt cttctgcatc cgattggttt    12240
gctccgcggt actccgtgcg cgccctacca ttcaccctga gcaattacag aagatcctat    12300
gaggcctttc tttctcagtg ccaggtggat attcccacct ggggaactag acatcccctg    12360
gggatgcttt ggcaccataa ggtgtcaacc ctgattgatg aaatggtgtc gcgtcggatg    12420
taccgcacca tggaaaaagc aggacaggct gcctggaaac aggtggtgag cgaggccacg    12480
ctgtctcgca ttagtggttt ggatgtggtg gctcattttc agcatcttgc cgccattgaa    12540
gccgagacct gtaaatattt ggcctctcgg ctgcccatgc tacacaatct gcgcatgaca    12600
gggtcaaatg taaccatagt gtataatagt actttgaatc aggtgtttgc tattttttcca   12660 acccctggat cccggccaaa gcttcatgat tttcagcaat ggctaatagc tgtgcactcc    12720
tccatatttt cctccgttgc ggcttcttgt actctttttg ttgtgctgtg gttgcggatt    12780
ccaatgctac gtactgtttt tggtttccgc tggttagggg caatttttcc ttcgaactca    12840
cggtgaatta cacggtgtgt ccgccttgcc tcacccggca agcagccgct gaggtctacg    12900
aaccaggcag gtctctttgg tgcaggatag ggcatgaccg atgtagtgag gaagaccatg    12960
acgatctagg gttcatggtt ccgtctggcc tctccagcga aggccacttg accagtgttt    13020
acgcctggtt ggcgttcctg tccttcagct acacggccca gttccatccc gagatatttg    13080
ggatagggaa tgtgagtcaa gtttatgttg acatcaagca ccaattcatc tgcgccgttc    13140
acgacgggga gaacgccacc ttgcctcgtc atgacaatat tcagccgta tatcagacct     13200 actaccaaca tcaagtcgac ggcggcaatt ggtttcacct agaatggctg cgcccctct     13260 tttcctcttg gttggtttta aatgtttctt ggtttctcag gcgttcgcct gcaagccatg    13320
tttcagttca agtctttcgg acatcaaaac caacacaacc gcagcatcag gctttgttgt    13380
cctccaggac atcagctgcc ttaggcatgg cgactcgtcc tctcagacga ttcgcaaaag    13440
ctctcagtgc cgcgcggcga tagggacgcc cgtgtacatc actgtcacag ccaatgtcac    13500
agatgagaat tatttacatt cttctgatct ccttatgctt tcttcttgcc ttttctatgc    13560
ttctgagatg agtgaaaagg gattcaaggt gatgtttggc aatgtgtcag gcatcgtggc    13620
tgtgtgtgtc aactttacca gctacgtcca acatgtcaag gagtttaccc aacgctcctt    13680
ggtggtcgat catgtgcggc tgctccattt catgacacct gagaccatga ggtgggcaac    13740
cgttttagcc tgttttcttg ccatcttact ggcaatttga atgttcaagt atgttgggga    13800
gatgcttgac cgcgggctgt tgctcgcgat tgctttcttt gtggtgtatc gtgccatttt    13860
gttttgctgc gctcgtcaac gccaacagca acagcagctc tcatcttcag ttaatttaca    13920
acttgacgct atgtgagctg aatggcacag attggctgaa agacaaattt gattgggcat    13980
tggagacttt tgtcatcttt cccgtgttga ctcacattgt ctcatatagt gcactcacca    14040
ctagccattt ccttgacaca gtcggtctgg ttactgtgtc tactgccggg ttctaccacg    14100
ggcggtatgt tctgagtagc atctacgcgg tctgcgctct ggccgcattg acttgcttcg    14160
tcattaggct tgcgaagaac tgcatgtcct ggcgctactc ttgtaccaga tatactaact    14220
tccttctgga cactaagggc agactctatc gctggcggtc gcccgttatc atagagaaag    14280
ggggtaaggt tgaggtcgaa ggtcacctga tcgacctcaa aagagttgtg cttgatggtt    14340
ccgtggcaac ccctttaacc agagtttcag cggaacaatg gggtcgtctt tagacgactt    14400
ttgctatgat agcacggctc cacaaaaggt gcttttggcg ttttccatta cctacacgcc    14460
agtgatgata tatgctctaa aggtaagtcg cggccgactt ttagggcttc tgcacctttt    14520
gatctttctg aattgtactt ttaccttcgg gtacatgaca tgcgtgcact ttaatagcac    14580
```

-continued

```
aaataaggtc gcgctcacta tgggagcagt agttgcactt ctttgggggg tgtactcagc    14640
catagaaacc tggaagttca tcacctccag atgtcgtttg tgcttgctag gccgcaagta    14700
cattctggcc cccgcccacc acgtcgaaag tgccgcgggc tttcatccga tcgcggcaaa    14760
tgataaccac gcatttgtcg tccggcgtcc cggctccact acggttaacg gcacattggt    14820
gcccggggttg aaaagcctcg tgttgggtgg cagaaaagct gttaaacagg gagtggtaaa    14880
ccttgtcaaa tatgccaaat aacaacggca agcagcaaaa gaaaagagg gggaatggcc     14940
agccagtcaa tcagctgtgc cagatgctgg gtaagatcat cgcccagcaa aaccagtcca    15000
gaggcaaggg accgggggaag aaaattaaga ataaaaaccc ggagaagccc cattttcctc    15060
tagcgactga agatgacgtc aggcatcact tcacccctag tgagcggcaa ttgtgtctgt    15120
cgtcgatcca gactgccttt aaccagggcg ctggaacctg taccctatca gattcaggta    15180
ggataagtta cactgtggag tttagtttgc cgacgcatca tactgtgcgc ctgatccgcg    15240
tcacagcgcc atcatcagcg taatgggctg gcattcctta agcacctcag tgttagaatt    15300
ggaagaatgt gtggtgaatg gcactgattg gcactgtgcc tctaagtcac ctattcaatt    15360
agggcgaccg tgtggggggtt aagtttaatt ggcgagaacc atgcggccga aattaaaaaa    15420
aaaa                                                                  15424

<210> SEQ ID NO 2
<211> LENGTH: 15424
<212> TYPE: DNA
<213> ORGANISM: Porcine reproductive and respiratory syndrome virus

<400> SEQUENCE: 2
tcgcccgggc aggtgttggc tctatgcctt ggcatttgta ttgtcaggag ctgcgaccat      60
tggtacagcc caaaactagc tgcacagaaa acgcccttct gtgacagccc tcttcagggg     120
agcttagggg tctgtcccta gcaccttgct tccggagttg cactgcttta cggtctctcc     180
aacccttttaa ccatgtctgg gatacttgat cggtgcacgt gcaccccccaa tgccagggtg    240
tttatggcgg agggccaagt ctactgcaca cgatgtctca gtgcacggtc tctccttcct     300
ctgaatctcc aagttcctga gcttggagtg ctgggcctat tttacaggcc cgaagagcca     360
ctccggtgga cgttgccacg tgcattcccc actgttgagt gctcccccgc cggggcctgc     420
tggctttctg cgatctttcc aattgcacga atgaccagtg gaaacctgaa cttttcaacaa    480
agaatggtgc gggtcgcagc tgagattttac agagccggcc agctcacccc tgcagtcttg    540
aaggctctac aagtttatga acggggttgc cgctggtacc ctatagtcgg acctgtccct    600
ggagtggccg ttttttgccaa ctccctacat gtgagtgata aacctttccc gggagcaact    660
catgtgctaa ccaacctgcc actcccgcag aggcctaagc ctgaagactt ttgcccttttt    720
gagtgtgcta tggctgacgt ctatgatatt ggtcatggcg ccgtcatgta tgtggccaaa    780
gggaaagtct cctgggcccc tcgtggcggg gatgaggcga aatttgaaac tgtccctagg    840
gagttgaagt tgatcgcgaa ccaactccac atctccttcc cgccccacca cgcagtggac    900
atgtctaagt tgtgttcat agcccctggg agtggtgtct ctatgcgggt cgagtgccca    960
cacggctgtc tccccgctaa tactgtccct gaaggtaact gctggtggcg cttgtttgac    1020
tcgctcccac tggacgttca gaacaaagaa attcgccgtg ccaaccaatt cggctatcaa    1080
accaagcatg gtgtcgctgg caagtaccta caacggaggc tgcaagctaa tggtctccga    1140
gcagtgactg atacagatgg acccattgtc gtacagtatt tctctgttag ggagagctgg    1200
```

```
atccgccact tcagactggc ggaagagcct agcctccctg ggtttgaaga cctcctcaga   1260
ataagggtag agcccaatac gtcgccattg agtgacaagg gtggaaaaat cttccggttt   1320
ggcagtcaca aatggtacgg tgctggaaag agagcaagga aagcacgctc tggtatgacc   1380
accacagtcg ctcaccgcgc cttgcccgct cgtgaaatcc agcaagccaa aaagcacgag   1440
gatgccggcg ctgataaggc tgtgcatctc aggcactatt ctccgcctgc cgacgggaac   1500
tgtggttggc actgcatttc cgccatcgcc aaccgaatgg tgaattccaa atttgaaact   1560
actcttcccg agagggtgag accttcagat gactgggcta ctgacgagga ccttgtgaac   1620
accatccaaa ttctcaagct ccctgcggcc ttggacagga acggtgcttg tgttggcgcc   1680
aaatacgtgc ttaagctgga aggcgagcat tggactgtct ctgtgaccct gggatgtcc    1740 ccttctttgc tccccttga atgtgttcag ggctgttgtg agcataagag cggacttggt    1800
cccccagatg cggtcgaagt tttcggattt gaccctgcct gccttgaccg actggctgag   1860
gtaatgcact tgcctagcag tgtcatccca gctgctctgg ccgaaatgtc cggcgacccc   1920
aactgtccgg cttccccggt cactactgtg tggactgttt cacaattctt tgcccgccac   1980
agaggaggag agcaccctga tcaggtgcgc ttaggaaaaa tcatcagcct ttgtcaagtt   2040
gttgaggaat gctgttgcca tcagaataaa accaaccggg ccaccccgga agaggttgcg   2100
gcaaggattg atcagtacct ccatggtgca acaagtcttg aagaatgctt gattaggctt   2160
gagagggttt gcccgccgag cgctgcggac accttctttg attggaatgt tgtgctccct   2220
ggggttgggg cttcaactca gacaaccaaa cagctccatg tcaaccagtg ccgcgctctg   2280
gttcctgtcg tgactcaaga gcctttggac aaagactcag tccctctgac cgccttctcg   2340
ctgtccaatt gctactatcc tgcacaaggt gacgaggttc gtcaccgtga gaggctaaac   2400
tccgtactct ctaagctgga gggggttgtt cgtgaggaat atgggctcac gccaactgaa   2460
cctggcccgc gacccgcact accgaacggg ctcgtcgaac ttaaagacca gatggaggag   2520
gatctgctga aactagtcaa cgcccaggca acttcagaaa tgatggcctg gcagccgag    2580 caggttgatc tgaaagcttg ggtcaaaaac tacccacggt ggacaccgcc accccctcca   2640
ccaagagttc agcctcgaaa aacaaagtct gtcaagagct tgccagggaa caaacctgtc   2700
cccgctccac gcaggaaggt cagatctgat tgtggcagcc cgattttgat gggcgacaat   2760
gttcctgacg gtcgggaaga tttgactgtt ggtggccccc ttgatctttc gacaccatcc   2820
gagccgatga cacctctgag tgagcctgca cttatgccc gcgttgcaata tatttctagg   2880 ccagtgacat ctttgagtgt gctggcccca gttcctgcac cgcgtagaac tgtgtcccga   2940
ccggtgacgc ccttgagtga gccaattttt gtgtctgcac cgcgacacaa atttcagcag   3000
gtggaagaag cgaatctggc ggcaacaacg ctgacgcacc aggacgaacc tctagatttg   3060
tctgcatcct cacagactga atatgaggct tctccctaa caccactgca gaacatgggt   3120
attctggagg tggggggca agaagctgag gaagttctga gtgaaatctc ggatacactg   3180
aatgacatca accctgcacc tgtgtcatca agcagctccc tgtcaagtgt taagatcaca   3240
cgcccaaaac actctgctca agccatcatt gactcgggcg ggcctgcag tgggcatctc   3300 cgaagggaaa aagaagcatg cctcagcatc atgcgtgagg cttgtgatgc ggctaagctt   3360
agtgaccctg ccacgcagga atggcttct cgcatgtggg ataggttga catgctgact   3420 tggcgcaaca cgtctgctta ccaggcgttc cgcatcttag atggtaggtt tgagtttctc   3480
ccaaagatga tactcgagac accgccgccc tacccgtgtg ggtttgtgat gctgcctcac   3540
acgcctgcac cttccgtggg tgcagagagt gaccttacca ttggttcagt cgccactgaa   3600
```

-continued

```
gatgttccac gcatcctcgg gaaaatagaa acgccggcg agatgcccaa ccagggcrc    3660
ttgacatcct tcggggaaga accggtgtgc gaccaacctg tcaaggactc ctggatgtcg    3720
tcgcggggt ttgacgagag cacaacggct ccgtccgctg gtacaggtgg tgctgactta    3780
cccaccgatt tgccaccttc agatggtttg gatgcggacg agtgggggcc gttacggacg    3840
gtaagaaaga aagctgaaag gctcttcgac caattgagcc gtcaggtttt taacctcgtc    3900
tcccatctcc ctgttttctt ctcacacctc ttcaaatctg acagtggtta ttctccgggt    3960
gattggggtt ttgcagcttt tactttattt tgcctctttt tgtgttacag ctacccattc    4020
tttggttttg ttcccctctt gggtgttttt tctgggtctt ctcggcgtgt gcgcatgggg    4080
gtttttggct gttggttggc ttttgctgtt ggcctgttca agcctgtgtc cgacccagtc    4140
ggcactgctt gtgagtttga ctcgccagag tgtaggaacg tccttcattc ttttgagctt    4200
ctcaaacctt gggaccctgt tcgcagcctt gttgtgggcc ccgtcggtct cggccttgcc    4260
attcttggca ggttactggg cggggcacgc tacatctggc attttttgct taggcttggc    4320
attgttgcag attgtatctt ggctggagct tatgtgcttt ctcaaggtag gtgtaaaaag    4380
tgctggggat cttgtgtaag aactgctcct aatgaaatcg ccttcaacgt gttccctttt    4440
acgcgtgcga ccaggtcgtc actcatcgac ctgtgcgatc ggttttgtgc gccaaaaggc    4500
atggacccca ttttcctcgc tactgggtgg cgcgggtgct ggaccggccg aagtcccatt    4560
gagcaaccct ctgaaaaacc catcgcgttc gcccagttgg atgaaaagag gattacggct    4620
agaactgtgg gcgctcagcc ttatgatcct aaccaagccg taaagtgctt gcgggtgtta    4680
caggcgggtg gggcgatagt ggccgaggca gtcccaaaag tggtcaaggt ttccgctatt    4740
ccattccgag ctcccttttt tcccaccgga gtgaaggttg atcctgagtg caggatcgtg    4800
gtcgaccccg acacttttac tacagctctc cggtctggtt actccaccac aaacctcgtc    4860
cttggtgtgg gggactttgc ccaactgaat ggattaaaaa tcaggcaaat ttccaagccc    4920
tcggaggag gcccgcacct cattgctgcc ctgcatgttg cttgctcgat ggcgttgcac    4980
atgcttgctg gagtttatgt aactgcagtg gggtcttgcg gtaccggcac caacgatccg    5040
tggtgcacta acccattcgc cgtccctggc tacggacctg gctccctctg cacgtccaga    5100
ttgtgcatct cccaacatgg ccttaccctg cccttgacag cacttgtggc aggattcggt    5160
cttcaggaaa ttgccctagt cgttttgatt ttcgtttcca tcggaggcat ggctcatagg    5220
ttgagttgta aggctgatat gctgtgcgtc ttacttgcaa tcgccagcta tgtttggta    5280
ccccttacct ggttgctctg tgtgtttcct tgctggttgc gctggttctc tttgcaccct    5340
ctcaccattc tatggttggt gttttcttg atgtctgtaa atatgccttc gggaatctta    5400
accgtggtgt tattggttgc tctttggctt ctaggccgtt atactaatgt tgttggtctt    5460
gttacccct atgatattca tcattacacc aatggcccc gcggtgttgc cgccttggct    5520
accgcaccag atgggactta cttggccgct gtccgccgcg ctgcgttgac tggccgcacc    5580
gtgctgttta cccgtctca gcttgggtcc cttcttgagg gcgctttcag aactcgaaag    5640
ccctcactga acaccgtcaa tgtggtcggg tcctccatgg gctctggcgg agtgttcact    5700
atcgatggga aaattaagtg cgtgactgcc gcacatgtcc ttacgggtaa ttcagccagg    5760
gtttccgggg tcggcttcaa tcaaatgctt gactttgatg taaaagggga cttcgccata    5820
gctgattgcc cgaattggca aggggctgct cctaagaccc aattctgcga ggatggatgg    5880
actggccgcg cctattggct gacatcctct ggcgtcgaac ccggtgtcat tgggaatgga    5940
```

```
ttcgccttct gcttcaccgc gtgcggcgat tccgggtccc cagtgatcac cgaagccggt    6000
gagcttgtcg gcgttcacac aggatcaaac aaacaaggag gaggcattgt tacgcgcccc    6060
tctggccagt tttgcaatgt ggcacccatc aagctgagcg aattaagtga gttcttttgct   6120 ggacctaagg tcccgctcgg tgatgtgaag gttggcagcc acataattaa agacatatgc    6180
gaggtacctt cagatctttg cgccttgctt gctgccaaac ccgaactgga aggaggcctc    6240
tccaccgtcc aacttctgtg tgtgtttttc ctcctgtgga gaatgatggg acatgcctgg    6300
acgcccttgg ttgctgttgg gttttttatc ttgaatgagg ttctcccagc tgtactggtc    6360
cggagtgttt tctcctttgg aatgtttgtg ctatcttggc tcacaccatg gtctgcgcaa    6420
gttctgatga tcaggcttct aacagcagct cttaacagga acagattgtc actcgccttt    6480
tacagccttg gtgcagcgac cggttttgtc gcagatctgg cggcaactca agggcacccg    6540
ttgcaggcag taatgaattt aagtacctat gccttcctgc ctcggataat ggtcgtgacc    6600
tcaccagtcc cagtgattgc gtgtggtgtt gtgcacctcc ttgccataat tttgtacttg    6660
tttaagtacc gctgcctgca caatgtcctt gttggcgatg gtgcgttctc tgcggctttc    6720
ttcttgcgat actttgccga ggggaaattg agggaagggg tgtcgcaatc ctgcgggatg    6780
aatcatgagt cgctgactgg tgccctcgct atgagactta atgacgagga cttggatttt    6840
cttacgaaat ggactgattt taagtgtttt gtttctgcat ccaacatgag gaatgcggcg    6900
ggccagttca tcgaggctgc ctatgctaaa gcacttagaa ttgaacttgc ccagttggtg    6960
caggttgata aggttcgagg tactttggcc aaacttgaag cttttgctga taccgtggca    7020
ccccaactct cgcccggtga cattgttgtt gctcttggcc atacgcctgt tggcggtatc    7080
ttcgacctaa aggttggtag caccaagcat accctccaag ccattgagac cagagttctt    7140
gccgggtcca aaatgaccgt ggcgcgtgtc gttgatccaa cccccacacc cccacccgca    7200
cccgtgccta tccccttcc accgaaagtt ctggagaatg gtcccaacgc ctgggggggat    7260 gaggatcgtt tgaataagaa gaagaggcgc aggatggaag ccgtcggcat ctttgttatg    7320
ggtggaaaga aatatcagaa attttgggac aagaactccg gtgatgtgtt ttatgaggag    7380
gtccatgata acacagacgc gtgggagtgc ctcagagttg acaaccctgc cgactttgac    7440
cctgagaagg gaactctgtg cgggcatact accattgaag ataagactta cagtgtctac    7500
gcctccccat ctggcaagaa attcctggtc cccgtctacc cagagagcaa aaaaaaccaa    7560
tgggaagctg cgaagctttc cgtggaacag gcccttggca tgatgaatgt cgacggtgaa    7620
ctgacagcca aagaagtgga gaaactgaaa agaataattg acaaactcca gggcctgact    7680
aaggagcagt gtttaaactg ctagccgcca gcggcttgac ccgctgtggt cgcggcggct    7740
tggttgttac tgagacagcg gtaaaaatag tcaaatttca caaccggacc ttcaccctag    7800
gacctgtgaa tttaaaagtg gccagtgagg ttgagctaaa agacgcggtc gagcataacc    7860
aacacccggt tgcaagaccg gttgatggtg tgttgtgct cctgcgctcc gcagttcctt    7920
cgcttataga cgtcttaatc tccggcgctg atgcatctcc caagttactc gcccgccacg    7980
ggccgggaaa cactgggatc gatggcacgc tttgggattt tgaggccgag gccactaaag    8040
aggaaattgc actcagtgcg caaataatac aggcttgtga cattaggcgc ggcgacgcac    8100
ctgaaattgg tcttccttat aagctgtacc ctgtcagggg caaccctgag cgggtaaaag    8160
gagttttaca gaatcaaagg tttgagagca taccttataa aacccccagt gacactggaa    8220
gcccagtgca cgcggctgcc tgcctcacgc ccaatgccac tccggtgact gatgggcgct    8280
ccgtcttggc cacgactatg ccctccggtt ttgagttgta tgtaccgacc attccagcgt    8340
```

```
ctgtccttga ttatcttgat tctaggcctg actgccccaa acagttgaca gagcacggct   8400
gtgaggacgc cgcattaaga gacctctcca agtatgactt gtccacccaa ggctttgttt   8460
tacctggagt tcttcgcctt gtgcgtaagt acctgtttgc tcatgtgggt aagtgcccgc   8520
ccgttcatcg gccttccact taccctgcca agaattctat ggctggaata aatgggaaca   8580
ggtttccaac caaggacatc cagagcgtcc ctgaaatcga cgttctgtgc gcacaggccg   8640
tgcgggaaaa ctggcaaact gttacccctt gtaccctcaa gaaacagtat tgtgggaaga   8700
agaagactag gacaatactc ggcaccaata acttcattgc gctggcccac cgggcagcgt   8760
tgagtggtgt cacccagggc ttcatgaaaa aggcgtttaa ctcgcccatt gccctcggta   8820
aaaacaaatt taaagagctt cagactccgg tcttaggcag gtgccttgaa gctgatcttg   8880
catcctgcga tcgctccaca cctgcaattg tccgctggtt tgccgccaat cttctttatg   8940
aacttgcctg tgctgaagag cacctgccgt cgtacgtgtt gaactgctgc cacgacctac   9000
tggtcacgca gtccggcgca gtaactaaga gaggtggcct gtcgtctggc gacccgatca   9060
cttctgtgtc caacaccatt tacagcttgg tgatatatgc acaacacatg gtgctcagtt   9120
actttaaaag tggtcaccct catggccttc tgtttctaca agaccagctg aagtttgagg   9180
acatgctcaa ggttcaaccc ctgatcgtct attcggacga cctcgtactg tatgccgagt   9240
ctcccaccat gccaaactac cactggtggg ttgaacatct gaacctgatg ctgggttttc   9300
agacggaccc aaagaagaca gccataacag actcgccatc atttctaggc tgtaggataa   9360
taaatggacg ccagctcgtc cctaaccgtg acaggattct cgcggccctc gcctaccata   9420
tgaaggcaag caatgtctct gaatactacg cctcggcggc tgcgatactc atggacagct   9480
gtgcttgttt agagtatgat cccgaatggt ttgaagagct tgtagttggg atagcgcagt   9540
gtgcccgcaa ggacggctac agttttcccg gcccgccgtt cttcttgtcc atgtgggaaa   9600
aactcagatc caatcatgag gggaagaagt ccagaatgtg cggggtactgc ggggccccgg   9660 ctccgtacgc cactgcctgt ggcctcgacg tctgtattta ccacacccac ttccaccagc   9720
attgtccagt catcatctgg tgtggccacc cggctggttc tggttcttgt agtgagtgca   9780
aaccccccct agggaaaggc acaagccctc tagatgaggt gttagaacaa gtcccgtata   9840
agcctccacg gactgtaatc atgcatgtgg agcagggtct caccctctt gacccaggca   9900 gataccagac tcgccgcgga ttagtctccg ttaggcgtgg cattagagga aatgaggttg   9960
atctaccaga cggtgattat gctagcaccg ccctactccc tacttgtaaa gagattaaca   10020
tggtcgctgt cgcctctaat gtgttgcgca gcaggttcat catcggcccg cctggtgctg   10080
ggaaaacata ctggctcctt caacaggtcc aggatggtga tgtcatttac acgccaactc   10140
accagaccat gctcgatatg attagggctt tggggacgtg ccggttcaac gtcccagcag   10200
gtacgacgct gcaattccct gccccctccc gtaccggccc ttgggttcgc atcctagccg   10260
gcggttggtg tcctggcaag aattccttcc tggatgaagc agcgtattgt aatcaccttg   10320
atgtcttgag gcttcttagc aaaactaccc tcacctgtct gggagatttc aaacaactcc   10380
acccagtggg tttttgattct cattgctatg tttttgacat catgcctcag actcaactga   10440
agaccatctg gagatttgga cagaatatct gtgatgccat tcagccagat tacagggaca   10500
aacttgtatc catggtcaac acaacccgtg taacctacgt ggaaaaacct gtcaagtatg   10560
ggcaagtcct cacccctttac cacagggacc gagaggacgg cgccatcaca attgactcca   10620
gtcaaggcgc cacatttgat gtggttacac tgcatttgcc cactaaagat tcactcaaca   10680
```

```
ggcaaagagc ccttgttgct attaccaggg caagacatgc tatctttgtg tatgacccac    10740
acaggcaact gcagagcatg tttgatcttc ctgcgaaagg cacacccgtc aacctcgctg    10800
tgcaccgtga cgagcagctg atcgtgctag atagaaataa caaagaatgc acggttgctc    10860
aggctctagg caatggggat aaattcaggg ccacagacaa gcgcgttgta gattctctcc    10920
gcgccatttg tgcagatctg gaagggtcga gctccccgct cccaaggtc gcacacaact    10980 tgggatttta tttctcgcct gatttgacac agtttgctaa actcccggta gaacttgcac    11040
cccactggcc cgtggtgaca acccagaaca atgaaaagtg gccagaccgg ttggttgcta    11100
gccttcgccc cgtccataag tatagccgcg cgtgcatcgg tgccggctac atggtgggcc    11160
cctcagtgtt tctgggcacc cctggggttg tgtcatacta tctcacaaaa tttgtcaggg    11220
gcgaggctca aatgcttccg gagacagtct tcagcaccgg ccgaattgag gtagattgcc    11280
gtgagtatct tgatgaccgg gagcgagaaa ttgctgagtc cctcccccat gctttcattg    11340
gcgacgtcaa aggcactacc gttggaggat gtcaccatgt cacctccaaa taccttccgc    11400
gcttccttcc caaggaatca gtcgcggtag tcggggtttc aagccccggg aaagccgcaa    11460
aagcagtttg cacattaaca gatgtgtatc tcccagatct cgaagcttac ctccacccag    11520
agacccagtc caagtgctgg aaaatgatgt tggacttcaa ggaagttcga ctgatggtct    11580
ggaaggacaa gacggcctat tttcaacttg aaggccgcca tttcacctgg taccagcttg    11640
caagctatgc ctcgtacatc cgagttcctg ttaactctac ggtgtatttg gacccctgca    11700
tgggccctgc cctttgcaac agaagagttg tcgggtccac tcattgggga gctgacctcg    11760
cagtcacccc ttatgattac ggtgccaaaa tcatcctgtc tagtgcatac catggtgaaa    11820 tgcccccctgg gtacaaaatc ctggcgtgcg cggagttctc gcttgacgat ccagtgaggt    11880
acaaacacac ctgggggttt gaatcggata cagcgtatct gtacgagttc accggaaacg    11940
gtgaggactg gaggattac aatgatgcgt ttcgtgcgcg ccagaaaggg aaaatttata    12000
aggccactgc caccagcatg aggtttcatt ttcccccggg ccctgtcatt gaaccaactt    12060
taggcctgaa ttgaaatgaa atgggtcca tgcaaagcct ctttgacaaa attggccaac    12120
tttttgtgga tgcttttcacg gaattttggg tgtccattgt tgatatcatc atattttttgg    12180 ccattttgtt tggcttttacc atcgctggct ggctggtggt cttctgcatc cgattggttt    12240
gctccgcggt actccgtgcg cgccctacca ttcaccctga gcaattacag aagatcctat    12300
gaggcctttc tttctcagtg ccaggtggat attcccacct ggggaactag acatcccctg    12360
gggatgtttt ggcaccataa ggtgtcaacc ctgattgatg aaatggtgtc gcgtcggatg    12420
taccgcacca tggaaaaagc aggacaggct gcctggaaac aggtggtgag cgaggccacg    12480
ctgtctcgca ttagtggttt ggatgtggtg gctcattttc agcatcttgc cgccattgaa    12540
gccgagacct gtaaatattt ggcctctcgg ctgcccatgc tacacaatct gcgcatgaca    12600
gggtcaaatg taaccatagt gtataatagt actttgaatc aggtgtttgc tattttttcca    12660 accctggat cccggccaaa gcttcatgat tttcagcaat ggctaatagc tgtgcactcc    12720
tccatatttt cctccgttgc ggcttcttgt actctttttg ttgtgctgtg gttgcggatt    12780
ccaatactac gtactgtttt tggtttccgc tggttagggg caattttttcc ttcgaactca    12840 cggtgaatta cacggtgtgt ccgccttgcc tcacccggca agcagccgct gaggtctacg    12900
aaccaggcag gtctctttgg tgcaggatag gcatgaccg atgtagtgag gacgaccatg    12960
acgatctagg gttcatggtt ccgcctggcc tctccagcga aggccacttg accagtgttt    13020
acgcctggtt ggcgttcctg tccttcagct acacggccca gttccatccc gagatatttg    13080
```

```
ggatagggaa tgtgagtcaa gtttatgttg acatcaagca ccaattcatc tgcgccgttc   13140
acgacgggga gaacgccacc ttgcctcgtc atgacaatat ttcagccgta tttcagacct   13200
actaccaaca tcaagtcgac ggcggcaatt ggtttcacct agaatggctg cgccccttct   13260
tttcctcttg gttggtttta aatgtttctt ggtttctcag gcgttcgcct gcaagccatg   13320
tttcagttca agtctttcgg acatcaaaac caacactacc gcagcatcag gctttgttgt   13380
cctccaggac atcagctgcc ttaggcatgg cgactcgtcc tctcagacga ttcgcaaaag   13440
ctctcagtgc cgcgcggcga tagggacgcc cgtgtacatc actgtcacag ccaatgtcac   13500
agatgagaat tatttacatt cttctgatct ccttatgctt tcttcttgcc ttttctatgc   13560
ttctgagatg agtgaaaagg gattcaaggt gatatttggc aatgtgtcag gcatcgtggc   13620
tgtgtgtgtc aactttacca gctacgtcca acatgtcaag gagtttaccc aacgctcctt   13680
ggtggtcgat catgtgcggc tgctccattt catgacacct gagaccatga ggtgggcaac   13740
cgttttagcc tgtttttttg ccatcttact ggcaatttga atgttcaagt atgttgggga   13800
gatgcttgac cgcgggctgt tgctcgcgat tgctttcttt gtggtgtatc gtgccatttt   13860
gttttgctgc gctcgtcaac gccaacagca acagcagctc tcatcttcag ttgatttaca   13920
acttgacgct atgtgagctg aatggcacag attggctgaa agacaaattt gattgggcag   13980
tggagacttt tgtcatcttt cccgtgttga ctcacattgt ctcatatggt gcactcacca   14040
ctagccattt ccttgacaca gtcggtctgg ttactgtgtc taccgccggg ttctaccacg   14100
ggcggtatgt tctgagtagc atctacgcgg tctgcgctct ggccgcattg atttgcttcg   14160
tcattaggct tgcgaagaac tgcatgtcct ggcgctactc ttgtaccaga tatactaact   14220
tccttctgga cactaagggc agactctatc gctggcggtc gcccgttatc atagagaaag   14280
ggggtaaggt tgaggtcgaa ggtcacctga tcgacctcaa aagagttgtg cttgatggtt   14340
ccgtggcaac cccttaacc agagtttcag cggaacaatg gggtcgtctt tagacgactt   14400
ttgctatgat agcacggctc cacaaaaggt gcttttggcg ttttccatta cctacacgcc   14460
agtgatgata tatgctctaa aggtaagtcg cggccgactt ttagggcttc tgcaccttt   14520 gatcttctg aattgtactt ttaccttcgg gtacatgaca ttcgtgcact ttaatagcac   14580
aaataaggtc gcgctcacta tgggagcagt agttgcactt ctttgggggg tgtactcagc   14640
catagaaacc tggaagttca tcacctccag atgccgtttg tgcttgctag gccgcaagta   14700
cattctggcc cccgcccacc acgtcgaaag tgccgcgggc tttcatccga tcgcggcaaa   14760
tgataaccac gcatttgtcg tccggcgtcc cggctccact acggttaacg gcacattggt   14820
gcccgggttg aaaagcctcg tgttgggtgg cagaaaagct gttaaacagg gagtggtaaa   14880
ccttgtcaaa tatgccaaat aacaacggca agcagcaaaa gaaaagagg gggaatggcc   14940 agccagtcaa tcagctgtgc cagatgctgg gtaagatcat cgcccagcaa aaccagtcca   15000
gaggcaaggg accggggaag aaaattaaga ataaaaaccc ggagaagccc catttcctc   15060 tagcgactga agatgacgtc aggcatcact tcaccctag tgagcggcaa ttgtgtctgt   15120
cgtcgatcca gactgccttt aaccaggcg ctggaacctg taccctatca gattcagta   15180 ggataagtta cactgtggag tttagtttgc gacgcatca tactgtgcgc ctgatccgcg   15240
tcacagcgcc atcatcagcg taatgggctg gcattcctta agcacctcag tgttagaatt   15300
ggaagaatgt gtggtgaatg gcactgattg gcactgtgcc tctaagtcac ctattcaatt   15360
```

-continued

```
agggcgaccg tgtgggggtt aagtttaatt ggcgagaacc atgcggccga aattaaaaaa  15420
aaaa                                                                15424
```

PORCINE REPRODUCTIVE AND RESPIRATORY SYNDROME VACCINE, BASED ON ISOLATE JA-142

RELATED APPLICATION

This is a continuation of application Ser. No. 09/461,879, filed Dec. 15, 1999, which is a continuation-in-part of application Ser. No. 09/298,110 filed Apr. 22, 1999, now abandoned.

SEQUENCE LISTING

A printed Sequence Listing accompanies this application. In accordance with 37 CFR 1.821(a)(2)(e), it is requested that the previously submitted compliant sequence listing in computer readable format be transferred from application Ser. No. 09/461,879 to this application.

BACKGROUND OF THE INVENTION

1. Field of the Invention

The present invention is broadly concerned with attenuated avirulent atypical porcine reproductive and respiratory syndrome (PRRS) virus (PRRSV), and corresponding live virus vaccines for administration to swine in order to confer effective immunity in the swine against PRRSV. The invention also includes methods of immunizing swine against PRRSV, and a new, highly efficient method of passaging viruses to attenuation.

2. Description of the Prior Art

PRRS emerged in the late 1980's as an important viral disease of swine. PRRSV causes severe reproductive failure in pregnant sows, manifested in the form of premature farrowings, increased numbers of stillborn, mummified and weak-born pigs, decreased farrowing rate, and delayed return to estrus. Additionally, the respiratory system of swine infected with PRRSV is adversely affected, which is evidenced by lesions that appear in the lungs of infected swine. To combat the problems associated with PRRSV infection, vaccines have been developed which conferred immunity to then extant PRRSV strains.

Epidemics of an unusually severe form of PRRS, referred to hereafter as "atypical PRRS", were first recognized in North America in the latter part of 1996. They differed from epidemics of "typical PRRS" in that: 1) clinical signs were more prolonged as well as more severe; 2) the incidence of abortion was greater, especially during early and middle gestation; 3) there was a higher incidence of gilt and sow mortality; 4) PRRSV was less often isolated from aborted fetuses, stillborn pigs, and liveborn pigs —perhaps because abortions were more often the result of acute maternal illness rather than transplacental infection; 5) lung lesions of young affected pigs were more extensive; and 6) commercially available vaccines provided little or no protection. Collectively these observation indicated the emergence of more virulent and antigenically distinct strains of PRRSV and the need for a new generation of PRRS vaccines.

The most frequently used method for producing attenuated, live-virus vaccine is to serially passage the virus in a substrate (usually cell culture) other than the natural host (S) until it becomes sufficiently attenuated (i.e., reduced in virulence or diseases-producing ability) to be used as a vaccine. For the first passage, a cell culture is infected with the selected inoculum. After obtaining clear evidence of virus replication (e.g., virus-induced cytopathic effects [CPE] in the infected cells), an aliquot of the cell culture medium, or infected cells, or both, of the first passage are used to infect a second cell culture. The process is repeated until one or more critical mutations in the viral genome cause sufficient attenuation so that the virus can be safely used as a vaccine. The degree of attenuation is usually determined empirically by exposing the natural host (S) to progressively greater passage levels of the virus.

The above procedure is fundamentally sound and has been successfully used for the development of numerous vaccines for human and veterinary use. However, it is relatively inefficient because the logarithmic phase of virus replication, during which mutations are most likely to occur, is often completed long before evidence of virus replication becomes visibly obvious.

Therefore, there is a decided need in the art for a vaccine that confers effective immunity against PRRSV strains, including recently discovered atypical PRRSV strains. There is also a need in the art for a method of making such a vaccine. Finally, what is needed is a method of passaging a virus that attenuates the virus more efficiently than was heretofore thought possible with the resulting attenuated virus eliciting PRRSV specific antibodies in swine thereby conferring effective immunity against subsequent infection by PRRSV.

SUMMARY OF THE INVENTION

The present invention overcomes the problems outlined above, and provides attenuated, atypical PRRSV strains, and corresponding improved modified-live vaccines which confer effective immunity to newly discovered atypical PRRSV strains. "Effective immunity" refers to the ability of a vaccine to prevent swine PRRSV infections, including atypical PRRSV infections, which result in substantial clinical signs of the disease. That is to say, the immunized swine may or may not be serologically positive for PRRSV, but do not exhibit any substantial clinical symptoms. "Atypical PRRSV" refers to these new strains of PRRSV that are substantially more virulent than typical PRRSV strains.

In preferred forms, the vaccine of the invention includes live virus which has been attenuated in virulence. The resulting attenuated virus has been shown to be avirulent and to confer effective immunity. A particularly virulent strain of atypical PRRS (denominated JA-142) which caused especially severe symptoms of PRRS and represents the dominant strain of atypical PRRSV, was chosen for subsequent attenuation through passaging. The resultant attenuated virus has been deposited in the American Type Culture Collection (ATCC), Rockville, Md. on Feb. 2, 1999, and was accorded ATCC Accession No. VR-2638. This attenuated virus is a preferred Master Seed Virus (MSV) which has been subsequently passaged and developed as an effective PRRSV vaccine.

The name given the unattenuated virus, JA-142, arises from the restriction enzyme pattern. The 1 represents the inability of the enzyme MLU I to cleave the virus in open reading frame 5 (ORF 5). The 4 represents cleavage by Hinc II at base pair positions 118 and 249 of ORF 5 and short contiguous sequences. The 2 represents cleavage by Sac II at base pair position 54 of ORF 5 and short contiguous sequences.

Passaging of the virus to attenuation was accomplished using a novel method which resulted in increased efficiency. Specifically, the virus was kept in the logarithmic phase of replication throughout multiple cell culture passages in order to materially shorten the time to attenuation. This is achieved by ensuring that in each cell culture there is a substantial excess of initially uninfected cells relative to the number of virus present. Thus, by transferring only small numbers of virus from passage-to-passage, logarithmic replication is assured.

In practice, the process is normally initiated by inoculation of several separate cell cultures with progressively smaller viral aliquots (i.e., lesser numbers of virus in each culture.) For example, starting cultures could contain 200 μl, 20 μl and 2 μl viral aliquots. After an initial short incubation period (e.g., 24 hours), the same viral aliquots (in the example, 200 μl, 20 μl and 2 μl) from each cell culture are transferred to individual fresh (previously uninfected) cultures, while the starting cultures are monitored until cytopathic effect (CPE) is or is not observed. This process is continued in serial order for multiple passages, using the same viral aliquots in each case and preserving the cultures for CPE observation. If all of the serial culture passages exhibit CPE after a selected number of passages are complete, the larger viral aliquot series may be terminated (in the example 200 μl and 20 μl), whereupon another series of progressively smaller viral aliquots are employed (e.g., 2 μl, 0.2 μl and 0.02 μl) and the process is again repeated, again keeping the cell cultures after transfer for CPE observation.

At some point in this successively smaller viral aliquot inoculation process, CPE will not be observed in a given cell culture. When this occurs, the next higher viral aliquot level showing CPE is substituted for the passage in which CPE was not observed, whereupon subsequent passages will be inoculated using previously employed viral aliquots.

Inasmuch as a virus will tend to become more efficient at infecting cells and also replicate to a higher infectivity titer for cell cultures over time, (which is especially true with RNA viruses such as PRRSV), it will be seen that smaller and smaller viral aliquots are required to maintain infection during serial transfer. The use of the smallest aliquot that maintains infection helps to assure that viral replication remains in a logarithmic phase throughout the process.

The DNA sequence of the attenuated passaged virus from the 201st passage was then determined using conventional methods. The sequence of this attenuated virus was designated as MSV JA-142 Passage No. 201, the sequence of which is given as SEQ ID No. 1. The sequence of the virulent virus, JA-142, is given as SEQ ID No. 2.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); ComputerAnalysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403–410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3'terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Preferably, sequences sharing at least about 75%, more preferably at least about 85%, still more preferably at least about 90% and most preferably at least about 95% sequence homology with SEQ ID No. 1 are effective as conferring immunity upon animals vaccinated with attenuated viruses containing such homologous sequences. Alternatively, sequences sharing at least about 65%, more preferably at least about 75%, still more preferably at least about 85%, and most preferably at least about 95% sequence identity with SEQ ID No. 1 are also effective at conferring immunity upon animals vaccinated with attenuated viruses containing such identical sequences.

DETAILED DESCRIPTION OF THE PREFERRED EMBODIMENT

The following examples set forth preferred embodiments of the present invention. It is to be understood, however, that these examples are provided by way of illustration and nothing therein should be taken as a limitation upon the overall scope of the invention.

EXAMPLE 1

Materials and Methods

This example describes a passage method of attenuating viruses which maximizes attenuation efficiency by ensuring that the virus is preferably in a logarithmic phase of replication. Virus was passed (i.e. an aliquot of nutrient medium including the virus, unattached cells, and cell debris from a virus-infected cell culture was added to the nutrient medium of a noninfected culture) at daily intervals. Different amounts of virus were added at each interval by using multiple cultures. For example, at the beginning, 200 µl was transferred to one noninfected culture, 20 µl was added to a second noninfected culture, and 2 µl to a third noninfected culture. The goal was to have a sufficient amount of susceptible cells so that the replication cycles could continue until the next transfer. The procedure was deemed successful if the cells eventually showed CPE. However, because PRRSV-induced CPE do not appear until sometime after the logarithmic growth phase, passages were made before it was known whether or not they would be ultimately successful ("blind passages"). Passages that resulted in virus induced CPE were said to have resulted in a "take". If a passage did not result in a take, the passage was restarted using the highest dilution from the last passage which did result in a take. As more and more passages were made, the virus became more adapted to replicate in the cell line and less able to produce disease symptoms in its original host. These changes occur through random mutations that occur during replication.

Using this method, the following procedures were used to passage an exemplary virus in accordance with the present invention, MSV, JA-142. This strain was passaged in MARC-145 cell cultures at daily intervals. Twenty-four-well plates were used for the process to minimize the amount of cells and nutrient medium required, and to simplify the multiple-aliquot passage technique. Cells and nutrient medium were added to each well and the cells were allowed to form, or nearly form (greater than about 70%), a confluent monolayer. The nutrient medium comprised approximately 90% Earle's balanced salt solution minimal essential medium (MEM), 10% fetal calf serum and 0.05 mgm/ml of gentamicin sulfate. The volume of nutrient medium used was approximately 1 ml. Usually, three wells of a column were used for each amount of virus that was transferred. An aliquot of nutrient medium from the previous passage was transferred to the first well in the column at 48 or 72 hours, after the cell cultures had been prepared, nutrient medium from the first well was transferred to the second well of the same column at 72 or 96 hours and the third well of the same column at 96 or 120 hours. Plates were usually set up twice a week so sometimes the fourth well of the column was used and sometimes it was not used. Passaging conditions were maintained at 37° C. in a moist atmosphere containing 5% $CO_2$.

Different sized aliquots (having different amounts of virus) for each passage were tested to determine if the amount of virus was sufficient to induce CPE. For example, a separate series of aliquot transfers (passages) of 200 µl, 20 µl, and 2 µl, respectively, was used until the smaller aliquots consistently exhibited CPE with the goal being to transfer the smallest aliquot that produced CPE. When the smallest aliquot (e.g. 2 µl) of the group of aliquots being tested consistently resulted in CPE, smaller amounts were tested (e.g. 0.2 µl and 0.02 µl). When a certain dilution did not exhibit CPE, that series of cultures was restarted with the next lower amount which did result in CPE at that passage (i.e. if the 2 µl transfer was unsuccessful at producing CPE in the 25th passage but the 20 µl transfer in the 25th passage was successful, the 2 µl transfer was repeated using 20 µl with 2 µl transfers resuming for the 26th passage.)

Using this method, the smallest amount of virus necessary to transfer to obtain CPE was determined. Virus was passed successfully at daily intervals using the following amounts of virus-infected nutrient medium (which reflect the highest dilution [i.e., smallest aliquot] which resulted in CPE keeping in mind that other dilutions would also work):

| Passage Number | Amount Transferred |
| --- | --- |
| 3–21 | 200 µl |
| 22, 23 | 20 µl |
| 24–41 | 200 µl |
| 42–83 | 20/200 µl (alternating) |

-continued

| Passage Number | Amount Transferred |
| --- | --- |
| 84–90 | 20 µl |
| 91–112 | 2 µl |
| 113 | 0.2 µl |
| 114–116 | 2 µl |
| 117 | 0.2 µl |
| 118–120 | 2 µl |
| 121 | 0.2 µl |
| 122–124 | 2 µl |
| 125–167 | 0.2 µl |
| 168 | 0.02 µl |
| 169–171 | 0.2 µl |
| 172 | 0.02 µl |
| 173–175 | 0.2 µl |
| 176 | 0.02 µl |
| 177–179 | 0.2 µl |
| 180 | 0.02 µl |
| 181–183 | 0.2 µl |
| 184 | 0.02 µl |
| 185–187 | 0.2 µl |
| 188 | 0.02 µl |
| 189–191 | 0.2 µl |
| 192 | 0.02 µl |
| 193–195 | 0.2 µl |
| 196 | 0.02 µl |
| 197 | 0.2 µl |

Results and Discussion

The passaging of the virus using the above method resulted in an attenuated PRRSV, JA-142. As is apparent, the virus became more adapted to replicate in the cell culture and therefore required a smaller amount of virus-infected nutrient medium to be transferred as passaging continued. For transfers using a very small amount of virus-infected nutrient medium (e.g. 0.2 µl or 0.02 µl), a separate dilution was required. This dilution was accomplished by adding a small amount of virus-infected nutrient medium to a larger amount of nutrient medium. For example, to obtain a transfer of 0.2 µl, 2 µl of virus infected nutrient medium was added to 20 µl of nutrient medium and 2 µl of this dilution was added to the next culture in the series. Using this approach, the highest dilution which resulted in CPE was used and the time necessary for passaging the virus was minimized. Passaging at daily intervals ensured that the virus was always in a logarithmic phase of replication. Daily transferring also ensured that there was an adequate number of cells for virus replication.

Because the mutations (which are probably cumulative) that are likely to result in attenuation only occur during replication, there is no advantage to having substantially all cells infected and replication either proceeding at a slower rate or stopping before the next transfer. Based on previous studies of PRRSV, it was known that the replication cycle is about 8 hours, therefore, transferring a minimal amount of virus from virus-infected nutrient medium to uninfected nutrient medium at daily intervals results in the virus always having plenty of cells within which to replicate.

As can be readily appreciated, passaging using this method results in a savings of time that was heretofore thought impossible (i.e. each passage required less time). This is especially important when a high number of passages are required for adequate virus attenuation. If each passage, using old methods, was performed at a 3 day interval, a procedure requiring 200 passages would take 400 fewer days using the method of the present invention.

EXAMPLE 2

Materials and Methods

This example determined if passage 200 of PRRS Virus, JA-142, would revert in virulence when passed in the host animal six times. This study consisted of six groups. Five pigs from group 1 (principle group) were inoculated intra-nasally with PRRS MSV, JA-142 passage 200, while three pigs from group 1A, (control group) were inoculated intra-nasally with sterile diluent. The animals were provided commercial feed and water ad libitum throughout the study. Pigs of both treatment groups were monitored daily for clinical signs (appearance, respiratory, feces, etc.). After six days, the animals were weighed, bled and sacrificed. After scoring the lungs for lesions, lung lavages were collected from each animal. The lung lavages were frozen and thawed one time, and a pool was prepared using 2.0 ml of serum and 2.0 ml of lung lavage from each animal within a group to prepare Backpassage 1 and 1A, respectively. This pool was used to challenge (intra-nasally) the animals in group 2 and group 2A, respectively. This process was repeated for groups 3 and 3A through 6 and 6A. Animals in each group were housed in separate but identical conditions.

Following inoculation, blood samples were collected and body temperatures were monitored. Rectal temperatures were measured for each animal periodically from −1 DPE (days post exposure) to 6 DPE and averaged together with other animal temperatures from the same group. The health status of each animal was monitored daily for the duration of the study. Results were compiled and scored on a daily observation form. The scoring parameters are as follows:

1. Appearance
   normal = 0; depressed = 1; excited = 2; comatose/death = 30.
2. Respiration
   normal = 0; sneeze = 1; cough = 1; rapid/short = 2; labored = 3.
3. Feces
   normal = 0; dry = 1; loose = 2; fluid = 3.
4. Eyes
   normal = 0; watery = 1; matted = 2; sunken = 3.
5. Nostrils
   normal = 0; watery discharge = 1; red/inflamed = 2; crusted ulcers = 3.
6. Mouth
   normal = 0; slobbers = 2; ulcer = 3.
7. Activity
   NA
8. Appetite
   normal = 0; decreased = 1; anorexic (none) = 3.
9. Other Animals were also weighed prior to inoculation and at necropsy. Average weight gains for each group were calculated for comparison. PRRS Enzyme Linked Immuno-Absorbent Assays (ELISA) and serum neutralization (SN) assays were performed following the exposures of the animals with test and control articles. Attempts to isolate PRRSV from serum samples were performed on MA-104 cells. Prior to and following vaccination, total white blood cell counts were determined using COULTER COUNTER MODEL Z 1, Coulter Corp., Miami, Fla. At necropsy, the lungs of each animal were scored. Lung scoring was done by separating the lung into 7 sections and determining the percentage of lung involvement (the percentage of the lung area affected as shown by lesions or redness for each section and multiplying by the approximate area of the whole lung) that percentage of total lung area that the section encompasses. Parameters for lung scoring are as follows:

Left Apical Lobe % of involvement      X 0.10 = ___
Left Cardiac Lobe % of involvement     X 0.10 = ___

-continued

| | |
|---|---|
| Left Diaphragmatic Lobe % of involvement | X 0.25 = ___ |
| Right Apical Lobe % of involvement | X 0.10 = ___ |
| Right Cardiac Lobe % of involvement | X 0.10 = ___ |
| Right Diaphragmatic Lobe % of involvement | X 0.25 = ___ |
| Intermediate Lobe of Right Lung % of involvement | X 0.10 = ___ |
| Total (Sum of all values in the far right column) | = ___ |

Results and Discussion

Each group of pigs was monitored for six days following vaccination. Clinical scores were low in all groups. Clinical score results are given in Table 1.

TABLE 1

Daily Clinical Scores

| Treatment | Pig # | Day-1 | Day 0 | Day 1 | Day 2 | Day 3 | Day 4 | Day 5 | Day 6 | Average |
|---|---|---|---|---|---|---|---|---|---|---|
| | Group 1 | | | | | | | | | |
| JA-142 psg 200 | 545 | 0 | 0 | 2 | 0 | 0 | 0 | 0 | 0 | 0.25 |
| | 551 | 0 | 0 | 0 | 0 | 0 | 0 | 0 | 0 | 0 |
| | 561 | 0 | 0 | 0 | 0 | 0 | 0 | 0 | 0 | 0 |
| | 565 | 0 | 0 | 0 | 0 | 0 | 0 | 0 | 0 | 0 |
| | 806 | 0 | 0 | 0 | 0 | 0 | 0 | 0 | 0 | 0 |
| | Average | 0 | 0 | 0.4 | 0 | 0 | 0 | 0 | 0 | 0.05 |
| Saline | 550 | 0 | 0 | 0 | 0 | 0 | 0 | 0 | 0 | 0 |
| | 568 | 0 | 0 | 0 | 0 | 0 | 0 | 0 | 0 | 0 |
| | 801 | 0 | 0 | 0 | 0 | 0 | 0 | 0 | 0 | 0 |
| | Average | 0 | 0 | 0 | 0 | 0 | 0 | 0 | 0 | 0 |
| | Group 2 | | | | | | | | | |
| Backpassage 1 | 546 | 0 | 0 | 0 | 0 | 0 | 0 | 0 | 0 | 0 |
| | 553 | 0 | 0 | 0 | 0 | 0 | 0 | 0 | 0 | 0 |
| | 562 | 0 | 0 | 0 | 0 | 0 | 1 | 0 | 0 | 0.125 |
| | 572 | 0 | 0 | 0 | 0 | 0 | 0 | 0 | 0 | 0 |
| | 573 | 0 | 0 | 0 | 0 | 2 | 0 | 0 | 0 | 0.25 |
| | Average | 0 | 0 | 0 | 0 | 0.4 | 0.2 | 0 | 0 | 0.075 |
| Backpassage 1 | 556 | 0 | 0 | 0 | 0 | 0 | 0 | 0 | 0 | 0 |
| | 566 | 0 | 0 | 0 | 0 | 0 | 0 | 0 | 0 | 0 |
| | 802 | 0 | 0 | 0 | 0 | 0 | 0 | 0 | 0 | 0 |
| | Average | 0 | 0 | 0 | 0 | 0 | 0 | 0 | 0 | 0 |
| | Group 3 | | | | | | | | | |
| Backpassage 2 | 548 | 0 | 0 | 0 | 0 | 0 | 0 | 0 | 0 | 0 |
| | 567 | 0 | 0 | 0 | 0 | 0 | 0 | 0 | 0 | 0 |
| | 569 | 0 | 0 | 0 | 0 | 1 | 1 | 0 | 0 | 0.25 |
| | 574 | 0 | 0 | 0 | 0 | 0 | 0 | 0 | 0 | 0 |
| | 804 | 0 | 0 | 0 | 0 | 0 | 0 | 0 | 0 | 0 |
| | Average | 0 | 0 | 0 | 0 | 0.2 | 0.2 | 0 | 0 | 0.05 |
| Backpassage 2A | 547 | 0 | 0 | 0 | 0 | 0 | 0 | 0 | 0 | 0 |
| | 5564 | 0 | 0 | 0 | 0 | 0 | 0 | 0 | 0 | 0 |
| | 805 | 0 | 0 | 0 | 0 | 0 | 0 | 0 | 0 | 0 |
| | Average | 0 | 0 | 0 | 0 | 0 | 0 | 0 | 0 | 0 |
| | Group 4 | | | | | | | | | |
| Backpassage 3 | 549 | 0 | 0 | 0 | 0 | 0 | 0 | 0 | 0 | 0 |
| | 554 | 0 | 0 | 0 | 0 | 0 | 0 | 0 | 0 | 0 |
| | 563 | 0 | 0 | 0 | 0 | 0 | 0 | 0 | 0 | 0 |
| | 570 | 0 | 0 | 0 | 0 | 0 | 0 | 0 | 0 | 0 |
| | 803 | 0 | 0 | 0 | 0 | 0 | 0 | 0 | 0 | 0 |
| | Average | 0 | 0 | 0 | 0 | 0 | 0 | 0 | 0 | 0 |
| Backpassage 3A | 560 | 0 | 0 | 0 | 0 | 0 | 0 | 0 | 0 | 0 |
| | 571 | 0 | 0 | 0 | 0 | 0 | 0 | 0 | 0 | 0 |
| | 575 | 0 | 0 | 0 | 0 | 0 | 0 | 0 | 0 | 0 |
| | Average | 0 | 0 | 0 | 0 | 0 | 0 | 0 | 0 | 0 |
| | Group 5 | | | | | | | | | |
| Backpassage 4 | 1 | 0 | 2 | 0 | 0 | 2 | 0 | 2 | 2 | 1 |
| | 2 | 0 | 0 | 0 | 0 | 0 | 0 | 0 | 0 | 0 |
| | 3 | 2 | 0 | 2 | 2 | 2 | 2 | 2 | 2 | 1.75 |
| | 4 | 0 | 0 | 0 | 0 | 0 | 0 | 0 | 0 | 0 |
| | 5 | 0 | 0 | 0 | 0 | 0 | 0 | 0 | 0 | 0 |
| | Average | 0.4 | 0.4 | 0.4 | 0.4 | 0.8 | 0.4 | 0.8 | 0.8 | 0.55 |
| Backpassage 4A | 6 | 0 | 0 | 0 | 0 | 0 | 0 | 0 | 0 | 0 |
| | 7 | 0 | 0 | 2 | 2 | 2 | 2 | 2 | 2 | 1.5 |
| | 8 | 0 | 0 | 0 | 0 | 0 | 0 | 0 | 0 | 0 |
| | Average | 0 | 0.08 | 0.48 | 0.48 | 0.56 | 0.48 | 0.56 | 0.56 | 0.4 |

TABLE 1-continued

| Treatment | Pig # | Day-1 | Day 0 | Day 1 | Day 2 | Day 3 | Day 4 | Day 5 | Day 6 | Average |
|---|---|---|---|---|---|---|---|---|---|---|
| | Group 6 | | | | | | | | | |
| Backpassage 5 | 10 | 0 | 0 | 0 | 0 | 2 | 0 | 0 | 2 | 0.5 |
| | 12 | 0 | 0 | 0 | 2 | 2 | 0 | 0 | 2 | 0.75 |
| | 14 | 0 | 0 | 0 | 0 | 0 | 0 | 0 | 0 | 0 |
| | 15 | 2 | 2 | 2 | 0 | 0 | 0 | 0 | 2 | 1 |
| | 16 | 2 | 2 | 2 | 0 | 0 | 1 | 1 | 2 | 1.25 |
| | Average | 0.8 | 0.8 | 0.8 | 0.4 | 0.8 | 0.2 | 0.2 | 1.6 | 0.7 |
| Backpassage 5A | 9 | 0 | 0 | 0 | 0 | 0 | 0 | 0 | 0 | 0 |
| | 11 | 2 | 2 | 0 | 0 | 0 | 0 | 0 | 0 | 0.5 |
| | 13 | 0 | 0 | 0 | 0 | 0 | 0 | 0 | 0 | 0 |
| | Average | 0.666667 | 0.56 | 0.16 | 0.08 | 0.16 | 0.04 | 0.04 | 0.32 | 0.253333 |

There were no significant differences between groups for rectal temperatures or daily weight gains. All lung scores were negative.

Serologically, ELISA S/P ratios and SN titers were negative throughout each group's trial period. Virus isolation was attempted on all serum samples and lung lavages. By day 6, 60–100% of the serum samples from the groups given JA-142, passage 200, and subsequent back passes were positive. The groups given saline were negative. In the first three passes, virus was recovered in the lung lavages from only 20–40% of the pigs, but by the last three passes, the virus was recovered from 50–80% of the pigs.

Based on this data, JA-142 passage 200 did not revert to virulence when passed through pigs six times.

EXAMPLE 3

Materials and Methods

This example demonstrated that the level of attenuation of safety of MSV, JA-142, passage 200 did not change significantly during six backpassages in the host animal. Evaluation of level of attenuation or safety was performed using the pregnant sow model and monitoring the effect on reproductive performance. This model is the most sensitive test system and does not rely upon subjective factors for virulence testing. This example consisted of four groups (A, B, C & D) having seven sows per group. Group A was inoculated intra-nasally with PRRS MSV, JA-142 passage 200. Group B was inoculated intra-nasally with JA-142, passage 200, Backpassage 6. Group C was inoculated intra-nasally with sterile diluent, to act as normal controls. Group D was inoculated intra-nasally with PRRSV JA-142, passage 4. The test articles (challenge with JA-142, passage 4) were given at about 93 days gestation. Body temperatures of the sows were monitored for the first seven days following vaccination. Blood samples were collected from the sows once a week and at time of farrowing. Blood samples were collected and weights were recorded from piglets at birth, 7, and 14 days of age. The health status of each animal was monitored daily for the duration of the study up to and following farrowing for 14 days. The farrowing performance was evaluated by observing the health status of the piglets born.

PRRS ELISA assays were performed following the exposures of the sows with the test article. PRRS ELISA assays were also performed on the piglet sera weekly following farrowing. Following exposure to the test article, attempts to isolate PRRSV from serum samples were performed on MA-104 cells. Rectal temperatures were measured periodically from 0 days post vaccination (DPV) to 7 DPV and the average temperature of each group was determined. Prior to and after inoculation, total white blood cell counts were determined as in Example 1. Clinical observations of the sows, as in Example 2, were made from −1 DPV through farrowing. Clinical observations of the piglets were made from farrowing until 14 days of age. Finally, at necropsy, the lungs of each piglet were scored for percent lung involvement.

Results

The ELISA results indicate that the animals used in this study were naive to PRRSV. Those animals that received virus inocula, groups A, B, and D, sero-converted at 14 days post treatment. Three sows of group B remained negative at 14 days post treatment. At the time of farrowing, the negative sows of group B tested positive for antibody to PRRSV.

The pigs' ELISA results indicated that the majority of the piglets born to sows of group A and group B were sampled after they had nursed. Those pigs that were negative at zero days post farrowing (0 DPF) tested positive at 7 DPF. All pigs born to sows of group C tested sero-negative throughout the study. Only a few pigs were tested from group D, since the majority were either stillborn or mummies. Half of those pigs that were tested were sero-positive. This indicated that the sero-negative pigs were sampled prior to nursing or they were not capable of nursing. All piglets born to sows of group D died before 7 DPF. Isolations of PRRSV from the sows of groups A and B were sporadic. Although the results of the ELISA test indicated that these sows were successfully inoculated with the viral test articles, many remained negative for virus isolation from serum.

The majority of pigs born to sows from groups A and B tested positive for virus isolation during the performance of the study. The litter born to one sow of group A never tested positive and the litter born to one sow of group B had only two of eight piglets test positive for virus isolation. No virus was recovered from the piglets born to sows from group C. Virus was recovered from the majority (71%) of piglets born from sows of group D.

Post treatment rectal temperatures were unremarkable. The groups that were treated with either MSV, backpassage 6 or sterile diluent experienced no measurements exceeding 101.7° F. Group D, treated with JA-142, passage 4, had four (out of seven) sows that experienced temperatures that exceeded 102° F. with one sow reaching 103.4° F. for one of the days. The weight gain performance of the piglets born to sows of groups A (treated with MSV) and B (treated with MSV, backpassage 6) was greater than that of the pigs born to the control sows of group C. The average weight gain for the 14 day observation period was 7.9 lbs. For group A, it was 7.7 lbs; for group B and group C it was 6.9 lbs. The difference in the weight gain was not related to the size of the litter remaining at 14 days. The average litter sizes at 14 days post farrowing (DPF) were 9 for group A, 7 for group B, and 10 for group C. No pig born to the sows of group D survived beyond 3 DPF.

The white blood cell (WBC) counts for the sows of groups A, B, and C remained relatively constant. The average percentages of the pre-challenge values were equal to or greater than 92% for the duration of the observation period. Three sows of group D experienced WBC counts that were lower than the expected normal range ($7–20 \times 10^6$/ml).

The post inoculation clinical scores were unremarkable for the sows of groups A and B. Several sows of group C were observed to experience clinical signs over a period of several days. The majority of the clinical symptoms observed were in the category of decreased appetite, respiratory symptoms, and depression. One sow of group C died on trial day 31 of chronic bacterial pneumonia. Six of the seven sows of group D were observed to have clinical signs, primarily of varying degrees in severity, of lost appetite, ranging from decreased to anorexic. Results of the clinical scoring for the sows are given in Table 2.

TABLE 2

Sow Clinical Scores

| Treatment | Sow# | -3 | -2 | -1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
|  | 178 | 0 | 0 | 0 | 0 | 0 | 0 | 0 | 0 | 0 | 0 | 0 | 0 | 0 | 0 | 0 | 0 |
|  | 215 | 0 | 0 | 0 | 0 | 0 | 0 | 0 | 0 | 0 | 0 | 0 | 0 | 0 | 0 | 0 | 0 |
|  | 233 | 0 | 0 | 0 | 0 | 0 | 0 | 0 | 0 | 0 | 0 | 0 | 0 | 0 | 0 | 0 | 0 |
|  | 243 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0 | 0 | 0 | 0 | 0 | 0 | 0 | 0 | 0 |
|  |  | 13 | 14 | 15 | 16 | 17 | 18 | 19 | 20 | 21 | 22 | 23 | 24 | 25 | 26 | 27 | 28 |
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
|  | 178 | 0 | 2 | 0 | 0 | 0 | 0 | 0 | 0 | 0 | 0 | 0 | 0 | 0 | 0 | 0 | 0 |
|  | 215 | 0 | 0 | 0 | 0 | 0 | 0 | 0 | 0 | 0 | 0 | 0 | 0 | 0 | 0 | 0 | 0 |
|  | 233 | 0 | 0 | 0 | 0 | 0 | 0 | 0 | 0 | 0 | 0 | 0 | 0 | 0 | 0 | 0 | 0 |
|  | 243 | 0 | 2 | 0 | 0 | 0 | 0 | 0 | 0 | 0 | 0 | 0 | 0 | 0 | 0 | 0 | 0 |
|  | Avg. | 0 | 0.6 | 0 | 0 | 0 | 0 | 0 | 0 | 0 | 0 | 0 | 0 | 0 | 0 | 0 | 0 |
|  |  | 29 | 30 | 31 | 32 | 33 | 34 | 35 | 36 | 37 | 38 | 39 | 40 | 41 | 42 | 43 | 44 |
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
|  | 178 | 0 | 0 | 0 | 0 | 0 | 0 | 0 | 0 | 0 | 0 | 0 | 0 | 0 | 0 | 0 | 0 |
|  | 215 | 0 | 0 | 0 | 0 | 0 | 0 | 0 | 0 | 0 | 0 | 0 | 0 | 0 | 0 | 0 | 0 |
|  | 233 | 0 | 0 | 0 | 0 | 0 | 0 | 0 | 0 | 0 | 0 | 0 | 0 | 0 | 0 | 0 | 0 |
|  | 243 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0 | 0 | 0 | 0 | 0 | 0 | 0 | 0 | 0 |
| Treatment | Sow# | -3 | -2 | -1 | 0 | 1 | 2 | 3 | 4 | 5 | 6 | 7 | 8 | 9 | 10 | 11 | 12 |
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
|  | 135 | 0 | 0 | 0 | 0 | 0 | 0 | 0 | 0 | 0 | 0 | 0 | 0 | 0 | 0 | 0 | 0 |
|  | 149 | 0 | 0 | 0 | 0 | 0 | 0 | 0 | 0 | 0 | 0 | 0 | 0 | 1 | 1 | 1 | 1 |
|  | 209 | 0 | 0 | 0 | 0 | 0 | 0 | 0 | 0 | 0 | 0 | 0 | 0 | 0 | 0 | 0 | 0 |
|  | 212 | 0 | 0 | 0 | 0 | 0 | 0 | 0 | 0 | 0 | 0 | 0 | 0 | 0 | 0 | 0 | 0 |
|  | 226 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0 | 0 | 0 | 0 | 0 | 0 | 0.1 | 0.1 | 0.1 | 0.1 |
|  |  | 13 | 14 | 15 | 16 | 17 | 18 | 19 | 20 | 21 | 22 | 23 | 24 | 25 | 26 | 27 | 28 |
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
|  | 135 | 0 | 0 | 0 | 0 | 0 | 0 | 0 | 0 | 0 | 0 | 0 | 0 | 0 | 0 | 0 | 0 |
|  | 149 | 0 | 0 | 0 | 0 | 0 | 0 | 1 | 1 | 0 | 0 | 0 | 0 | 0 | 0 | 0 | 0 |
|  | 209 | 0 | 0 | 0 | 0 | 0 | 0 | 0 | 0 | 0 | 0 | 0 | 0 | 0 | 0 | 0 | 0 |
|  | 212 | 0 | 0 | 0 | 0 | 0 | 0 | 0 | 0 | 0 | 0 | 0 | 0 | 0 | 0 | 0 | 0 |
|  | 226 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0.1 | 0.1 | 0 | 0 | 0 | 0 | 0 | 0 | 0 |
|  |  | 29 | 30 | 31 | 32 | 33 | 34 | 35 | 36 | 37 | 38 | 39 | 40 | 41 | 42 | 43 | 44 |
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
|  | 135 | 0 | 0 | 0 | 0 | 0 | 0 | 0 | 0 | 0 | 0 | 0 | 0 | 0 | 0 | 0 | 0 |
|  | 149 | 0 | 0 | 0 | 0 | 0 | 0 | 0 | 0 | 0 | 0 | 2 | 2 | 2 | 2 | 2 | 2 |
|  | 209 | 0 | 0 | 0 | 0 | 0 | 0 | 0 | 0 | 0 | 0 | 0 | 0 | 0 | 0 | 0 | 0 |

TABLE 2-continued

Sow Clinical Scores

|  | | | | | | | | | | | | | | | | | |
|---|---|---|---|---|---|---|---|---|---|---|---|---|---|---|---|---|---|
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0.3 | 0.3 | 0.3 | 0.3 | 0.3 | 0.3 |

| Treatment | Sow# | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group C | 58 | 0 | 0 | 0 | 0 | 0 | 0 | 0 | 0 | 0 | 0 | 0 | 0 | 0 | 0 | 0 | 0 |
| Sterile | 113 | 0 | 0 | 0 | 0 | 0 | 0 | 0 | 0 | 0 | 0 | 1 | 3 | 3 | 5 | 3 | 3 |
| Diluent | 117 | 0 | 0 | 0 | 0 | 0 | 0 | 0 | 0 | 0 | 0 | 0 | 0 | 0 | 0 | 1 | 1 |
| | 144 | 0 | 0 | 0 | 0 | 0 | 0 | 0 | 0 | 0 | 0 | 0 | 0 | 0 | 0 | 0 | 0 |
| | 156 | 0 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0.2 | 0.5 | 0.5 | 0.8 | 0.7 | 0.7 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group C | 58 | 0 | 0 | 0 | 0 | 0 | 0 | 0 | 0 | 0 | 0 | 0 | 0 | 0 | 0 | 0 | 0 |
| Sterile | 113 | 3 | 3 | 3 | 3 | 3 | 3 | 4 | 4 | 4 | 4 | 6 | 6 | 2 | 4 | 2 | 2 |
| Diluent | 117 | 0 | 0 | 0 | 0 | 0 | 0 | 1 | 5 | 5 | 5 | 5 | 5 | 2 | 4 | 1 | 1 |
| | 144 | 0 | 0 | 0 | 0 | 0 | 0 | 0 | 0 | 0 | 0 | 0 | 0 | 0 | 0 | 0 | 0 |
| | 156 | 2 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0.8 | 0.5 | 0.5 | 0.5 | 0.5 | 0.5 | 0.8 | 1.5 | 1.5 | 1.5 | 1.8 | 1.8 | 0.7 | 1.3 | 0.5 | 0.5 |

| | | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group C | 58 | 0 | 0 | 0 | 0 | 0 | 0 | 0 | 0 | 0 | 0 | 0 | 0 | 0 | 0 | 0 | 0 |
| Sterile | 113 | 2 | 2 | 30 | | | | | | | | | | | | | |
| Diluent | 117 | 2 | 2 | 0 | 0 | 0 | 0 | 0 | 0 | 0 | 0 | 0 | 0 | 0 | 0 | 0 | 0 |
| | 144 | 0 | 0 | 0 | 0 | 0 | 0 | 0 | 0 | 0 | 0 | 1 | 1 | 1 | 1 | 1 | 1 |
| | 156 | 0 | 0 | 0 | 0 | 0 | 0 | 0 | 0 | 0 | 0 | 0 | 0 | 0 | 0 | 0 | 0 |
| | 166 | 0 | 0 | 0 | 0 | 0 | 0 | 0 | 0 | 0 | 0 | 0 | 0 | 0 | 0 | 0 | 0 |
| | Avg. | 0.7 | 0.7 | 6 | 0 | 0 | 0 | 0 | 0 | 0 | 0 | 0.2 | 0.2 | 0.2 | 0.2 | 0.2 | 0.2 |

| Treatment | Sow# | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group D | 2 | 0 | 0 | 0 | 0 | 0 | 0 | 0 | 0 | 0 | 1 | 1 | 1 | 1 | 1 | 1 | 1 |
| JA-142 | 106 | 0 | 0 | 0 | 0 | 0 | 0 | 0 | 0 | 0 | 0 | 1 | 1 | 1 | 1 | 1 | 1 |
| Pass 4 | 159 | 0 | 0 | 0 | 0 | 0 | 0 | 0 | 0 | 0 | 3 | 1 | 1 | 1 | 1 | 1 | 1 |
| | 190 | 0 | 0 | 0 | 0 | 0 | 0 | 0 | 0 | 0 | 0 | 0 | 0 | 1 | 1 | 1 | 1 |
| | 206 | 0 | 0 | 0 | 0 | 0 | 0 | 0 | 0 | 0 | 0 | 1 | 1 | 0 | 0 | 0 | 0 |
| | 232 | 0 | 0 | 0 | 0 | 0 | 0 | 0 | 0 | 0 | 0 | 0 | 0 | 0 | 0 | 0 | 0 |
| | 234 | 0 | 0 | 0 | 0 | 0 | 0 | 0 | 0 | 0 | 0 | 0 | 0 | 0 | 1 | 1 | 1 |
| | Avg. | 0 | 0 | 0 | 0 | 0 | 0 | 0 | 0 | 0 | 0.6 | 0.6 | 0.6 | 0.6 | 0.7 | 0.7 | 0.7 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group D | 2 | 1 | 1 | 3 | 3 | 1 | 0 | 0 | 0 | 0 | 0 | 0 | 0 | 0 | 0 | 0 | 0 |
| JA-142 | 106 | 0 | 0 | 0 | 0 | 0 | 0 | 0 | 0 | 0 | 0 | 0 | 0 | 0 | 0 | 0 | 0 |
| Pass 4 | 159 | 1 | 1 | 1 | 1 | 3 | 4 | 2 | 3 | 3 | 3 | 2 | 0 | 0 | 2 | 0 | 0 |
| | 190 | 1 | 2 | 0 | 0 | 0 | 0 | 0 | 0 | 0 | 0 | 0 | 0 | 0 | 0 | 0 | 0 |
| | 206 | 0 | 0 | 0 | 0 | 0 | 0 | 0 | 0 | 0 | 0 | 0 | 0 | 0 | 0 | 0 | 0 |
| | 232 | 0 | 0 | 0 | 0 | 0 | 0 | 0 | 0 | 0 | 0 | 0 | 0 | 0 | 0 | 0 | 0 |
| | 234 | 0 | 2 | 0 | 0 | 0 | 0 | 0 | 0 | 0 | 0 | 0 | 0 | 0 | 0 | 0 | 0 |
| | Avg. | 0.4 | 0.3 | 0.6 | 0.6 | 0.6 | 0.6 | 0.3 | 0.4 | 0.4 | 0.4 | 0.3 | 0 | 0 | 0.3 | 0 | 0 |

| | | 29 | 30 | 31 | 32 | 33 | 34 | 35 | 36 | 37 | 38 |
|---|---|---|---|---|---|---|---|---|---|---|---|
| Group D | 2 | 0 | 0 | 0 | 1 | 1 | 1 | 3 | 3 | 1 | 1 |
| JA-142 | 106 | 0 | 0 | 0 | 0 | 0 | 0 | 0 | 0 | 0 | 0 |
| Pass 4 | 159 | 0 | 0 | 0 | 0 | 0 | 0 | 0 | 0 | 0 | 0 |
| | 190 | 0 | 0 | 0 | 0 | 0 | 0 | 0 | 0 | 0 | 0 |
| | 206 | 0 | 0 | 0 | 0 | 0 | 0 | 0 | 0 | 0 | 0 |
| | 232 | 0 | 0 | 0 | 0 | 0 | 0 | 0 | 0 | 0 | 0 |
| | 234 | 0 | 0 | 0 | 0 | 0 | 0 | 0 | 0 | 0 | 0 |
| | Avg. | 0 | 0 | 0 | 0.1 | 0.1 | 0.1 | 0.4 | 0.4 | 0.1 | 0.1 |

Clinical observations of the piglets fell into two major categories, death and reduced appetite. There were no significant differences between groups A, B and C in the area of average deaths per litter (DPL). Group A had an average of 1.3 DPL, group B had an average of 2.4 DPL, group C had an average of 2.0 DPL, and no pigs from group D survived beyond three days post farrowing. Clinical scores for the piglets are given in Table 3.

TABLE 3

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Group A JA-142 Pass 200 | 98 | 813 | 0 | 0 | 1 | 30 | | | | | | | | | | |
| | | 814 | 0 | 0 | 0 | 0 | 0 | 0 | 0 | 0 | 0 | 0 | 0 | 0 | 0 | 0 |
| | | 815 | 0 | 0 | 0 | 0 | 0 | 0 | 0 | 0 | 0 | 0 | 0 | 0 | 0 | 0 |
| | | 816 | 0 | 0 | 0 | 0 | 0 | 0 | 0 | 0 | 0 | 0 | 0 | 0 | 0 | 0 |
| | | 817 | 1 | 0 | 1 | 0 | 0 | 0 | 0 | 0 | 0 | 0 | 0 | 0 | 0 | 0 |
| | | 818 | 0 | 0 | 0 | 0 | 0 | 0 | 0 | 0 | 0 | 0 | 0 | 0 | 0 | 0 |
| | | 819 | 0 | 0 | 0 | 0 | 0 | 0 | 0 | 0 | 0 | 0 | 0 | 0 | 0 | 0 |
| | | 820 | 0 | 0 | 0 | 0 | 0 | 0 | 0 | 0 | 0 | 0 | 0 | 0 | 0 | 0 |
| | | 821 | 1 | 0 | 0 | 0 | 0 | 0 | 0 | 0 | 0 | 0 | 0 | 0 | 0 | 0 |
| | | 822 | 1 | 30 | | | | | | | | | | | | |
| | | Avg. | 0.3 | 3 | 0.2 | 3.3 | 0 | 0 | 0 | 0 | 0 | 0 | 0 | 0 | 0 | 0 |
| | 133 | 720 | 30 | | | | | | | | | | | | | |
| | | 721 | 0 | 1 | 0 | 0 | 0 | 0 | 0 | 0 | 0 | 0 | 0 | 0 | 0 | 0 |
| | | 722 | 0 | 0 | 0 | 1 | 0 | 0 | 0 | 0 | 0 | 0 | 0 | 0 | 0 | 0 |
| | | 723 | 0 | 0 | 0 | 0 | 0 | 0 | 0 | 0 | 0 | 0 | 0 | 0 | 0 | 0 |
| | | 724 | 0 | 1 | 0 | 0 | 0 | 1 | 0 | 0 | 0 | 0 | 0 | 0 | 0 | 0 |
| | | 725 | 0 | 0 | 0 | 0 | 0 | 0 | 0 | 0 | 0 | 0 | 0 | 0 | 0 | 0 |
| | | 798 | 0 | 0 | 0 | 0 | 0 | 0 | 0 | 0 | 0 | 0 | 0 | 0 | 0 | 0 |
| | | 799 | 30 | | | | | | | | | | | | | |
| | | 800 | 0 | 0 | 0 | 0 | 0 | 0 | 0 | 0 | 0 | 0 | 0 | 0 | 0 | 0 |
| | | 807 | 0 | 0 | 0 | 0 | 0 | 0 | 0 | 0 | 0 | 0 | 0 | 1 | 0 | 0 |
| | | 809 | 0 | 0 | 0 | 0 | 0 | 0 | 0 | 0 | 0 | 0 | 0 | 0 | 0 | 0 |
| | | 810 | 0 | 0 | 0 | 0 | 0 | 0 | 0 | 0 | 0 | 0 | 0 | 0 | 0 | 0 |
| | | 812 | 0 | 0 | 0 | 0 | 0 | 0 | 0 | 0 | 0 | 0 | 0 | 0 | 0 | 0 |
| | | Avg. | 4.6 | 0.2 | 0 | 0.1 | 0 | 0.1 | 0 | 0 | 0 | 0 | 0 | 0.1 | 0 | 0 |
| | 147 | 823 | 0 | 0 | 0 | 0 | 0 | 0 | 0 | 0 | 0 | 0 | 0 | 0 | 0 | 0 |
| | | 824 | 0 | 0 | 0 | 0 | 0 | 0 | 0 | 3 | 1 | 1 | 1 | 1 | 1 | 1 |
| | | 825 | 0 | 0 | 0 | 0 | 0 | 0 | 0 | 0 | 0 | 0 | 0 | 0 | 0 | 0 |
| | | 845 | 0 | 0 | 0 | 0 | 0 | 0 | 0 | 0 | 0 | 0 | 0 | 0 | 0 | 0 |
| | | 846 | 0 | 0 | 0 | 0 | 0 | 0 | 0 | 0 | 0 | 0 | 0 | 0 | 0 | 0 |
| | | 847 | 0 | 0 | 0 | 0 | 0 | 0 | 0 | 0 | 0 | 0 | 0 | 0 | 0 | 0 |
| | | 848 | 0 | 0 | 0 | 0 | 0 | 0 | 1 | 0 | 0 | 0 | 0 | 0 | 0 | 0 |
| | | 849 | 0 | 0 | 0 | 0 | 0 | 0 | 0 | 0 | 0 | 0 | 0 | 0 | 0 | 2 |
| | | 850 | 30 | | | | | | | | | | | | | |
| | | 976 | 0 | 0 | 0 | 0 | 0 | 0 | 0 | 0 | 0 | 0 | 0 | 0 | 0 | 0 |
| | | 977 | 0 | 0 | 0 | 0 | 1 | 1 | 3 | 30 | | | | | | |
| | | 978 | 30 | | | | | | | | | | | | | |
| | | Avg. | 5 | 0 | 0 | 0 | 0.1 | 0.1 | 0.4 | 3.3 | 0.1 | 0.1 | 0.1 | 0.1 | 0.1 | 0.3 |
| | 178 | 486 | 30 | | | | | | | | | | | | | |
| | | 487 | 0 | 0 | 0 | 0 | 0 | 0 | 0 | 0 | 0 | 0 | 0 | 1 | 0 | 0 |
| | | 488 | 0 | 0 | 0 | 0 | 0 | 0 | 0 | 0 | 0 | 0 | 0 | 0 | 0 | 0 |
| | | 489 | 0 | 0 | 0 | 0 | 0 | 0 | 0 | 0 | 0 | 0 | 0 | 0 | 0 | 0 |
| | | 490 | 0 | 0 | 0 | 0 | 0 | 0 | 0 | 0 | 0 | 0 | 0 | 0 | 0 | 0 |
| | | 491 | 0 | 0 | 0 | 0 | 0 | 0 | 0 | 0 | 0 | 0 | 0 | 0 | 0 | 0 |
| | | 492 | 0 | 0 | 0 | 0 | 0 | 0 | 0 | 0 | 0 | 0 | 0 | 0 | 0 | 0 |
| | | 493 | 0 | 0 | 0 | 0 | 0 | 0 | 0 | 0 | 0 | 0 | 0 | 0 | 0 | 0 |
| | | 494 | 0 | 1 | 0 | 0 | 0 | 0 | 0 | 0 | 0 | 0 | 0 | 0 | 0 | 0 |
| | | Avg. | 3.3 | 0.1 | 0 | 0 | 0 | 0 | 0 | 0 | 0 | 0 | 0 | 0.1 | 0 | 0 |
| Group A JA-142 Pass 200 | 215 | 495 | 0 | 0 | 0 | 0 | 0 | 0 | 0 | 0 | 0 | 0 | 0 | 0 | 0 | 0 |
| | | 496 | 0 | 0 | 0 | 0 | 0 | 0 | 0 | 0 | 0 | 0 | 0 | 0 | 0 | 0 |
| | | 497 | 0 | 0 | 0 | 0 | 0 | 0 | 0 | 0 | 0 | 0 | 0 | 0 | 0 | 0 |
| | | 498 | 0 | 0 | 0 | 0 | 0 | 0 | 0 | 0 | 0 | 0 | 0 | 0 | 0 | 0 |
| | | 499 | 0 | 0 | 0 | 0 | 0 | 0 | 0 | 0 | 0 | 0 | 0 | 0 | 0 | 0 |
| | | 500 | 0 | 0 | 0 | 0 | 0 | 0 | 0 | 0 | 0 | 0 | 0 | 0 | 0 | 0 |
| | | 808 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 233 | 476 | 0 | 0 | 0 | 0 | 0 | 0 | 0 | 0 | 0 | 0 | 0 | 0 | 0 | 0 |
| | | 477 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 480 | 0 | 0 | 0 | 0 | 0 | 0 | 0 | 0 | 0 | 0 | 0 | 0 | 0 | 0 |
| | | 481 | 0 | 0 | 0 | 0 | 0 | 0 | 0 | 0 | 0 | 0 | 0 | 0 | 0 | 0 |
| | | 482 | 0 | 0 | 0 | 0 | 0 | 0 | 0 | 0 | 0 | 0 | 0 | 0 | 0 | 0 |
| | | 483 | 0 | 0 | 0 | 0 | 0 | 0 | 0 | 0 | 0 | 0 | 0 | 0 | 0 | 0 |
| | | 484 | 0 | 0 | 0 | 0 | 0 | 0 | 0 | 0 | 0 | 0 | 0 | 0 | 0 | 0 |
| | | 485 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 243 | 707 | 0 | 0 | 0 | 0 | 0 | 0 | 0 | 0 | 0 | 0 | 0 | 0 | 0 | 0 |
| | | 708 | 0 | 0 | 0 | 0 | 0 | 0 | 0 | 0 | 0 | 0 | 0 | 0 | 0 | 0 |
| | | 709 | 0 | 0 | 0 | 0 | 0 | 0 | 0 | 0 | 0 | 0 | 0 | 0 | 0 | 0 |
| | | 710 | 0 | 0 | 0 | 0 | 0 | 0 | 0 | 0 | 0 | 0 | 0 | 0 | 0 | 0 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 711 | 0 | 0 | 0 | 0 | 0 | 0 | 0 | 0 | 0 | 0 | 0 | 0 | 0 | 0 |
| | | 712 | 0 | 0 | 0 | 0 | 0 | 0 | 0 | 0 | 0 | 0 | 0 | 0 | 0 | 0 |
| | | 713 | 0 | 0 | 0 | 0 | 0 | 0 | 0 | 0 | 0 | 1 | 30 | | | |
| | | 714 | 0 | 0 | 0 | 0 | 0 | 0 | 0 | 0 | 0 | 0 | 0 | 0 | 0 | 0 |
| | | 715 | 0 | 0 | 0 | 0 | 0 | 0 | 0 | 0 | 0 | 0 | 0 | 0 | 0 | 0 |
| | | 716 | 0 | 0 | 0 | 0 | 0 | 0 | 0 | 0 | 0 | 0 | 0 | 0 | 0 | 0 |
| | | 717 | 0 | 0 | 0 | 0 | 0 | 0 | 0 | 0 | 0 | 0 | 0 | 1 | 0 | 0 |
| | | 718 | 0 | 0 | 0 | 0 | 0 | 0 | 0 | 0 | 0 | 0 | 0 | 1 | 0 | 0 |
| | | 719 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0.1 | 2.3 | 0.2 | 0 | 0 |
| Group B | | | | | | | | | | | | | | | | |
| Backpassage 6 | 49 | 430 | 0 | 0 | 0 | 0 | 0 | 0 | 0 | 0 | 0 | 0 | 0 | 0 | 0 | 0 |
| | | 431 | 0 | 0 | 0 | 0 | 0 | 0 | 0 | 0 | 0 | 0 | 0 | 0 | 0 | 0 |
| | | 432 | 0 | 0 | 0 | 0 | 0 | 0 | 0 | 0 | 0 | 0 | 0 | 0 | 0 | 0 |
| | | 433 | 0 | 0 | 0 | 0 | 0 | 0 | 0 | 0 | 0 | 0 | 0 | 0 | 0 | 0 |
| | | 434 | 0 | 0 | 0 | 0 | 0 | 0 | 0 | 0 | 0 | 0 | 0 | 0 | 0 | 0 |
| | | 435 | 0 | 0 | 0 | 0 | 0 | 0 | 0 | 0 | 0 | 0 | 0 | 0 | 0 | 0 |
| | | 436 | 0 | 0 | 0 | 0 | 0 | 0 | 0 | 0 | 0 | 0 | 0 | 0 | 0 | 0 |
| | | 437 | 0 | 0 | 0 | 0 | 0 | 0 | 0 | 0 | 0 | 0 | 0 | 0 | 0 | 0 |
| | | 438 | 30 | 0 | 0 | 0 | 0 | 0 | 0 | 0 | 0 | 0 | 0 | 0 | 0 | 0 |
| | | Avg. | 3.3 | 0 | 0 | 0 | 0 | 0 | 0 | 0 | 0 | 0 | 0 | 0 | 0 | 0 |
| | 100 | 459 | 0 | 0 | 0 | 0 | 0 | 0 | 0 | 0 | 0 | 0 | 0 | 0 | 0 | 0 |
| | | 460 | 0 | 0 | 0 | 0 | 0 | 0 | 0 | 0 | 0 | 0 | 0 | 0 | 0 | 0 |
| | | 461 | 0 | 0 | 0 | 0 | 0 | 0 | 1 | 1 | 1 | 0 | 0 | 0 | 0 | 0 |
| | | 462 | 0 | 0 | 0 | 0 | 1 | 1 | 1 | 1 | 1 | 1 | 1 | 1 | 1 | 1 |
| | | 463 | 0 | 0 | 0 | 0 | 0 | 0 | 0 | 0 | 0 | 0 | 0 | 0 | 0 | 0 |
| | | 464 | 0 | 0 | 1 | 1 | 1 | 1 | 30 | | | | | | | |
| | | 465 | 0 | 30 | | | | | | | | | | | | |
| | | Avg. | 0 | 4.3 | 0.2 | 0.2 | 0.3 | 0.3 | 5.3 | 0.4 | 0.4 | 0.2 | 0.2 | 0.2 | 0.2 | 0.2 |
| | 135 | 439 | 0 | 0 | 0 | 0 | 0 | 0 | 0 | 30 | | | | | | |
| | | 440 | 0 | 0 | 0 | 0 | 0 | 0 | 0 | 0 | 0 | 0 | 0 | 0 | 0 | 0 |
| | | 441 | 0 | 0 | 0 | 0 | 0 | 0 | 0 | 0 | 0 | 0 | 0 | 0 | 0 | 0 |
| | | 442 | 0 | 0 | 0 | 1 | 1 | 1 | 1 | 1 | 1 | 1 | 3 | 3 | 3 | 30 |
| | | 443 | 0 | 0 | 0 | 0 | 0 | 0 | 0 | 0 | 0 | 0 | 0 | 0 | 0 | 0 |
| | | 444 | 0 | 0 | 0 | 0 | 0 | 0 | 1 | 1 | 0 | 0 | 0 | 0 | 0 | 0 |
| | | 445 | 0 | 0 | 0 | 0 | 0 | 0 | 0 | 0 | 0 | 0 | 0 | 0 | 0 | 0 |
| | | 446 | 0 | 0 | 0 | 0 | 0 | 0 | 0 | 0 | 0 | 0 | 0 | 0 | 0 | 0 |
| | | 447 | 0 | 0 | 0 | 0 | 0 | 0 | 0 | 0 | 0 | 0 | 0 | 0 | 0 | 0 |
| | | Avg. | 0 | 0 | 0 | 0.1 | 0.1 | 0.1 | 0.2 | 3.6 | 0.1 | 0.1 | 0.4 | 0.4 | 0.4 | 3.8 |
| | 149 | 231 | 0 | 0 | 0 | 0 | 0 | 0 | 0 | 0 | 0 | 0 | 0 | 0 | 0 | 0 |
| | | 232 | 0 | 0 | 0 | 0 | 0 | 0 | 0 | 0 | 0 | 0 | 0 | 0 | 0 | 0 |
| | | 233 | 0 | 0 | 0 | 0 | 0 | 0 | 30 | | | | | | | |
| | | 234 | 0 | 0 | 0 | 0 | 0 | 0 | 3 | 1 | 1 | 3 | 1 | 1 | 1 | 1 |
| | | 235 | 0 | 0 | 0 | 0 | 0 | 0 | 3 | 2 | 3 | 3 | 0 | 0 | 0 | 0 |
| | | 236 | 0 | 0 | 0 | 0 | 0 | 0 | 0 | 0 | 0 | 0 | 0 | 0 | 0 | 0 |
| | | 237 | 0 | 0 | 0 | 0 | 0 | 0 | 1 | 1 | 1 | 1 | 1 | 1 | 1 | 1 |
| | | 238 | 0 | 0 | 0 | 0 | 0 | 2 | 0 | 0 | 0 | 0 | 0 | 0 | 0 | 0 |
| | | 239 | 0 | 0 | 30 | | | | | | | | | | | |
| | | 240 | 30 | | | | | | | | | | | | | |
| | | 241 | 3 | 30 | | | | | | | | | | | | |
| | | 242 | 0 | 0 | 0 | 0 | 0 | 2 | 3 | 3 | 30 | | | | | |
| | | Avg. | 2.8 | 2.7 | 3 | 0 | 0 | 0.4 | 4.4 | 0.9 | 4.4 | 1 | 0.3 | 0.3 | 0.3 | 0.3 |
| Group B Backpassage 6 | 209 | 448 | 0 | 0 | 0 | 0 | 0 | 0 | 0 | 0 | 0 | 0 | 0 | 0 | 0 | 0 |
| | | 449 | 0 | 0 | 0 | 0 | 0 | 0 | 0 | 0 | 0 | 0 | 0 | 0 | 0 | 0 |
| | | 450 | 0 | 0 | 0 | 0 | 0 | 0 | 0 | 0 | 0 | 0 | 0 | 0 | 0 | 0 |
| | | 451 | 0 | 0 | 0 | 0 | 0 | 0 | 0 | 0 | 1 | 1 | 1 | 1 | 1 | 1 |
| | | 452 | 0 | 0 | 0 | 0 | 0 | 0 | 0 | 0 | 0 | 0 | 0 | 0 | 0 | 0 |
| | | 453 | 0 | 0 | 0 | 0 | 0 | 0 | 0 | 0 | 0 | 0 | 0 | 0 | 0 | 0 |
| | | 454 | 0 | 0 | 0 | 0 | 0 | 0 | 0 | 0 | 1 | 1 | 1 | 1 | 1 | 1 |
| | | 455 | 0 | 0 | 0 | 0 | 0 | 0 | 0 | 0 | 0 | 1 | 1 | 1 | 1 | 1 |
| | | 456 | 30 | | | | | | | | | | | | | |
| | | 457 | 0 | 0 | 0 | 0 | 0 | 0 | 0 | 0 | 2 | 1 | 1 | 1 | 1 | 1 |
| | | 458 | 30 | | | | | | | | | | | | | |
| | | Avg. | 5.5 | 0 | 0 | 0 | 0 | 0 | 0 | 0 | 0.4 | 0.4 | 0.4 | 0.4 | 0.4 | 0.4 |
| | 212 | 243 | 0 | 0 | 0 | 0 | 0 | 0 | 0 | 0 | 0 | 0 | 0 | 0 | 0 | 0 |
| | | 244 | 0 | 0 | 0 | 0 | 0 | 0 | 0 | 0 | 0 | 0 | 0 | 0 | 0 | 0 |
| | | 245 | 0 | 0 | 0 | 0 | 3 | 1 | 30 | | | | | | | |
| | | 246 | 0 | 0 | 0 | 0 | 0 | 0 | 0 | 0 | 0 | 0 | 0 | 0 | 0 | 0 |
| | | 247 | 0 | 0 | 0 | 0 | 0 | 2 | 2 | 0 | 0 | 0 | 0 | 0 | 0 | 0 |
| | | 248 | 0 | 0 | 0 | 0 | 2 | 0 | 0 | 0 | 0 | 0 | 0 | 0 | 0 | 0 |
| | | 249 | 0 | 0 | 0 | 0 | 0 | 0 | 2 | 2 | 0 | 0 | 2 | 0 | 0 | 0 |
| | | 250 | 0 | 0 | 0 | 3 | 30 | | | | | | | | | |
| | | 426 | 0 | 0 | 0 | 0 | 0 | 0 | 0 | 0 | 0 | 0 | 0 | 0 | 0 | 0 |
| | | 427 | 0 | 0 | 0 | 1 | 3 | 1 | 1 | 30 | | | | | | |
| | | 428 | 0 | 0 | 0 | 1 | 3 | 3 | 30 | | | | | | | |
| | | 429 | 0 | 0 | 0 | 0 | 2 | 3 | 3 | 3 | 3 | 3 | 3 | 1 | 30 | |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | 226 | Avg. Not Preg. | 0 | 0 | 0 | 0.4 | 3.6 | 0.9 | 6.2 | 3.9 | 0.4 | 0.4 | 0.6 | 0.1 | 3.8 | 0 |
| Group C | | | | | | | | | | | | | | | | |
| Sterile Diluent | 58 | 24 | 0 | 0 | 0 | 0 | 0 | 0 | 0 | 0 | 0 | 0 | 0 | 0 | 0 | 0 |
| | | 25 | 0 | 0 | 0 | 0 | 0 | 0 | 0 | 0 | 0 | 0 | 0 | 0 | 0 | 0 |
| | | 46 | 0 | 0 | 0 | 0 | 0 | 0 | 0 | 0 | 0 | 0 | 0 | 0 | 0 | 0 |
| | | 47 | 0 | 0 | 0 | 0 | 0 | 0 | 0 | 0 | 0 | 0 | 0 | 0 | 0 | 0 |
| | | 48 | 0 | 0 | 0 | 0 | 0 | 0 | 0 | 0 | 0 | 0 | 0 | 0 | 0 | 0 |
| | | 49 | 0 | 0 | 0 | 0 | 0 | 0 | 0 | 0 | 0 | 0 | 0 | 0 | 0 | 0 |
| | | 50 | 0 | 0 | 0 | 0 | 0 | 0 | 0 | 0 | 0 | 0 | 0 | 0 | 0 | 0 |
| | | 51 | 0 | 0 | 0 | 2 | 2 | 1 | 1 | 1 | 30 | | | | | |
| | | Avg. | 0 | 0 | 0 | 0.3 | 0.3 | 0.1 | 0.1 | 0.1 | 3.8 | 0 | 0 | 0 | 0 | 0 |
| | 113 | 17 | 30 | | | | | | | | | | | | | |
| | | 18 | 30 | | | | | | | | | | | | | |
| | | 19 | 30 | | | | | | | | | | | | | |
| | | 20 | 30 | | | | | | | | | | | | | |
| | | 21 | 0 | 30 | | | | | | | | | | | | |
| | | 22 | 30 | | | | | | | | | | | | | |
| | | 23 | 30 | | | | | | | | | | | | | |
| | | Avg. | 25.7 | 30 | | | | | | | | | | | | |
| | 117 | 52 | 1 | 0 | 0 | 0 | 0 | 0 | 0 | 0 | 0 | 0 | 0 | 0 | 0 | 0 |
| | | 53 | 0 | 0 | 0 | 0 | 0 | 0 | 0 | 0 | 0 | 0 | 0 | 0 | 0 | 0 |
| | | 54 | 0 | 0 | 0 | 0 | 0 | 0 | 0 | 0 | 0 | 0 | 0 | 0 | 0 | 0 |
| | | 55 | 0 | 0 | 0 | 0 | 0 | 0 | 0 | 0 | 0 | 0 | 0 | 0 | 0 | 0 |
| | | 56 | 1 | 0 | 0 | 0 | 30 | | | | | | | | | |
| | | 57 | 1 | 0 | 0 | 0 | 0 | 0 | 0 | 0 | 0 | 0 | 0 | 0 | 0 | 0 |
| | | 58 | 0 | 0 | 0 | 0 | 0 | 0 | 0 | 0 | 0 | 0 | 0 | 0 | 0 | 0 |
| | | 59 | 0 | 0 | 0 | 0 | 0 | 0 | 0 | 0 | 0 | 0 | 0 | 0 | 0 | 0 |
| | | 60 | 0 | 0 | 0 | 0 | 0 | 0 | 0 | 0 | 0 | 0 | 0 | 1 | 0 | 0 |
| | | 61 | 1 | 0 | 0 | 0 | 0 | 0 | 0 | 0 | 1 | 1 | 1 | 0 | 0 | 0 |
| | | 62 | 1 | 0 | 0 | 0 | 0 | 0 | 0 | 0 | 0 | 0 | 0 | 0 | 0 | 0 |
| | | Avg. | 0.5 | 0 | 0 | 0 | 2.7 | 0 | 0 | 0 | 0.1 | 0.1 | 0.1 | 0.1 | 0 | 0 |
| | 144 | 146 | 0 | 0 | 0 | 0 | 0 | 0 | 0 | 0 | 0 | 0 | 0 | 0 | 0 | 0 |
| | | 147 | 0 | 0 | 0 | 0 | 0 | 0 | 0 | 0 | 0 | 0 | 0 | 0 | 0 | 0 |
| | | 148 | 0 | 0 | 0 | 0 | 0 | 0 | 0 | 0 | 0 | 0 | 0 | 0 | 0 | 0 |
| | | 149 | 0 | 0 | 0 | 0 | 0 | 0 | 0 | 0 | 0 | 0 | 0 | 0 | 0 | 0 |
| | | 150 | 0 | 0 | 0 | 0 | 0 | 0 | 0 | 0 | 1 | 0 | 1 | 1 | 1 | 0 |
| | | 221 | 0 | 0 | 0 | 0 | 0 | 2 | 2 | 0 | 0 | 0 | 0 | 0 | 0 | 0 |
| | | 222 | 0 | 0 | 0 | 0 | 0 | 2 | 2 | 1 | 1 | 1 | 1 | 1 | 0 | 1 |
| | | 223 | 0 | 0 | 0 | 0 | 0 | 0 | 0 | 0 | 0 | 0 | 0 | 0 | 0 | 0 |
| | | 224 | 0 | 0 | 0 | 0 | 0 | 0 | 0 | 0 | 0 | 0 | 0 | 0 | 0 | 0 |
| | | 225 | 0 | 0 | 0 | 0 | 0 | 0 | 0 | 0 | 0 | 0 | 0 | 0 | 0 | 0 |
| | | 970 | 0 | 0 | 0 | 0 | 0 | 0 | 0 | 0 | 0 | 0 | 0 | 0 | 0 | 0 |
| | | 971 | 0 | 0 | 0 | 0 | 0 | 0 | 0 | 0 | 0 | 0 | 0 | 0 | 0 | 0 |
| | | Avg. | 0 | 0 | 0 | 0 | 0 | 0.3 | 0.3 | 0.1 | 0.2 | 0.1 | 0.2 | 0.2 | 0.1 | 0.1 |
| Group C Sterile Diluent | 156 | 63 | 0 | 0 | 0 | 0 | 0 | 0 | 0 | 0 | 0 | 0 | 0 | 0 | 0 | 0 |
| | | 64 | 0 | 0 | 1 | 0 | 30 | | | | | | | | | |
| | | 65 | 0 | 0 | 0 | 0 | 0 | 0 | 0 | 1 | 1 | 1 | 1 | 1 | 0 | 0 |
| | | 66 | 0 | 0 | 0 | 0 | 1 | 0 | 0 | 0 | 0 | 0 | 0 | 0 | 0 | 0 |
| | | 67 | 0 | 0 | 0 | 0 | 1 | 0 | 1 | 1 | 30 | | | | | |
| | | 68 | 0 | 0 | 0 | 0 | 0 | 0 | 0 | 0 | 0 | 0 | 0 | 0 | 0 | 0 |
| | | 69 | 0 | 0 | 0 | 0 | 0 | 0 | 0 | 1 | 0 | 0 | 0 | 0 | 0 | 0 |
| | | 70 | 0 | 0 | 0 | 0 | 0 | 0 | 0 | 0 | 0 | 0 | 0 | 0 | 0 | 0 |
| | | 71 | 0 | 0 | 0 | 0 | 0 | 2 | 2 | 0 | 0 | 0 | 0 | 0 | 1 | 0 |
| | | 72 | 0 | 0 | 0 | 0 | 0 | 0 | 0 | 0 | 0 | 0 | 0 | 0 | 0 | 0 |
| | | 73 | 0 | 0 | 0 | 0 | 0 | 0 | 0 | 0 | 0 | 0 | 0 | 0 | 0 | 0 |
| | | 74 | 0 | 0 | 0 | 0 | 1 | 0 | 0 | 0 | 0 | 0 | 0 | 0 | 0 | 0 |
| | | 75 | 0 | 0 | 0 | 0 | 0 | 0 | 0 | 0 | 0 | 0 | 0 | 0 | 0 | 0 |
| | | Avg. | 0 | 0 | 0.1 | 0 | 2.5 | 0.2 | 0.3 | 0.3 | 2.6 | 0.1 | 0.1 | 0.1 | 0.1 | 0 |
| | 166 | 76 | 0 | 0 | 0 | 0 | 0 | 0 | 0 | 0 | 0 | 0 | 0 | 0 | 0 | 0 |
| | | 77 | 0 | 0 | 0 | 0 | 0 | 0 | 0 | 0 | 0 | 0 | 0 | 0 | 0 | 0 |
| | | 78 | 0 | 0 | 0 | 0 | 0 | 0 | 0 | 0 | 0 | 0 | 0 | 0 | 0 | 0 |
| | | 79 | 0 | 0 | 0 | 0 | 0 | 0 | 0 | 0 | 0 | 0 | 0 | 0 | 0 | 0 |
| | | 80 | 0 | 0 | 0 | 0 | 0 | 0 | 0 | 0 | 0 | 0 | 0 | 0 | 0 | 0 |
| | | 81 | 1 | 0 | 0 | 0 | 0 | 0 | 0 | 0 | 0 | 0 | 0 | 0 | 0 | 0 |
| | | 141 | 0 | 0 | 0 | 0 | 0 | 0 | 0 | 0 | 0 | 0 | 0 | 0 | 0 | 0 |
| | | 142 | 0 | 0 | 0 | 0 | 0 | 0 | 0 | 0 | 0 | 0 | 0 | 0 | 0 | 0 |
| | | 143 | 0 | 0 | 0 | 0 | 0 | 0 | 0 | 0 | 0 | 0 | 0 | 0 | 0 | 0 |
| | | 144 | 0 | 0 | 0 | 0 | 0 | 0 | 0 | 0 | 0 | 0 | 0 | 0 | 0 | 0 |
| | | 145 | 1 | 30 | | | | | | | | | | | | |
| | | Avg. | 0.2 | 2.7 | 0 | 0 | 0 | 0 | 0 | 0 | 0 | 0 | 0 | 0 | 0 | 0 |
| Group D JA-142 Passage 4 | 2 | 891 | 1 | 3 | 30 | | | | | | | | | | | |
| | | 892 | 1 | 30 | | | | | | | | | | | | |
| | | Avg. | 1 | 16.5 | 30 | | | | | | | | | | | | |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | 106 | Aborted | NA | | | | | | | | | | | | | |
| | 159 | 883 | 30 | | | | | | | | | | | | | |
| | | 884 | 30 | | | | | | | | | | | | | |
| | | Avg. | 30 | | | | | | | | | | | | | |
| | 190 | Aborted | NA | | | | | | | | | | | | | |
| | 206 | 890 | 30 | | | | | | | | | | | | | |
| | | Avg. | 30 | | | | | | | | | | | | | |
| | 232 | 888 | 30 | | | | | | | | | | | | | |
| | | 889 | 30 | | | | | | | | | | | | | |
| | | Avg. | 30 | | | | | | | | | | | | | |
| | 234 | Aborted | NA | | | | | | | | | | | | | |

The farrowing performance results provided the most dramatic differences and similarities between the various treatment groups. Since the treatments would not have an effect on the size of the litters, the most appropriate way to compare the farrowing results would be by using percentage values. Group A had an average percentage of live/born of 85% (SD+/−9.6). Group B had an average percentage of live/born of 89% (SD+/−11.6). The control group (group C) had an average percentage of live/born of 83.4% (SD+/−7.9). The average percentages for stillborns for groups A, B and C were 8.8 (SD+/−9.66), 6.6 (SD+/−9.7), and 14 (SD +/−11.39), respectively. The average percentages of mummies born to sows of groups A, B, and C were 6.1 (SD+/−6.01), 3.9 (SD+/−4.45), and 2.6 (SD+/−4.01), respectively. The average percentages of live/born, stillborn and mummies born to the sows of group D were 8.7 (SD+/−8.92), 10.7 (SD+/−11.39), and 81.9 (SD+/−17.18), respectively.

The results of this example demonstrated the stability of the MSV, JA-142, passage 200 after being passed in the host animal six times. There were no significant differences between the group of sows treated with the MSV (group A) and those sows that were exposed to the Backpassage 6 virus (group B) in the categories of farrowing performance, leukopenia, rectal temperatures, and the clinical observations of either the sows or the piglets. In addition, the results in these same categories for the groups A and B were comparable to those achieved by group C that had been treated with sterile diluent. Finally, the performance of the sows that had been exposed to the virulent parent virus of MSV, JA-142, passage 4, clearly illustrated the level of attenuation of the MSV and the lack of reversion to virulence by the Backpassage 6, JA-142 virus.

EXAMPLE 4

Materials and Methods

This example evaluated the safety and level of attenuation of administering a 10×concentration of MSV, JA-142, passage 201. The study was performed on the pregnant sow model and monitored the effect of this dosage on reproductive performance. The study consisted of three groups, A, C, and D. Group A was inoculated intra-nasally with PRRS MSV, JA-142, passage 200. Group C was inoculated intra-nasally with sterile diluent, to act as a normal control group. Group D was inoculated intra-nasally with 1 OX JA-142, passage 201. All inoculations were given at about 93 days gestation. Body temperatures of the sows were monitored for the first seven days following inoculation (vaccination). Blood samples were collected from the sows once a week and at time of farrowing. Prior to and following inoculation, total white blood cell counts were determined as in Example 2. The health status of each animal was monitored daily for the duration of the study up to and following farrowing for 14 days. Clinical observations of the sows were made from −1 DPV through farrowing. The farrowing performance was evaluated by observing the health status of the piglets born. PRRSV ELISA assays were preformed following the exposures of the sows with the test article. Attempts to isolate PRRSV from serum samples were performed on MA-104 cells following exposure to the test article. Clinical observations of the piglets were made from farrowing until 14 days of age. Blood samples were collected from the piglets at birth, 7 and 14 days of age. PRRSV ELISA assays were performed on the piglet sera weekly following farrowing. Piglets were also weighed at birth, day 7 post farrowing, and at necropsy. At necropsy, the lungs of each piglet were scored for percent lung involvement.

Results and Discussion

There were no significant differences between groups given a 10×dose of MSV, JA-142, passage 201, groups given a regular dose of MSV, JA-142, passage 200, and groups given sterile diluent. Therefore, based on the safety and attenuation of MSV, JA-142, passage 200 and the lack of any significant difference in the results comparing these groups, a 10×dose of MSV, JA-142, passage 201 was shown to be safe, attenuated and effective in inducing antibodies against PRRSV.

EXAMPLE 5

Materials and Methods

This example demonstrated that a minimal vaccine dose of PRRSV, JA-142, passage 205, representing MSV+5, is efficacious in an experimental respiratory challenge model in feeder pigs. Pigs were divided into three groups. Group 1 was inoculated intramuscularly with PRRS MSV, JA-142, passage 205 at a titer of 2.0 logs/dose. Group 2 was inoculated intramuscularly with sterile diluent. Group 3 acted as normal controls. Pigs from groups 1 and 2 were challenged with a PRRSV isolate with an RFLP pattern of 144 on day 28 post vaccination. Body temperatures of the pigs were monitored for the first seven days following vaccination and daily following challenge. Each animal was weighed at vaccination, challenge, weekly throughout the study, and necropsy. Blood samples were collected weekly following vaccination and every two days following challenge. The health status of each animal was monitored daily for the duration of the study. At necropsy, each animal was sacrificed and the lungs were scored for percent lung involvement as in Example 2. PRRSV ELISA assays were performed following the exposures of the pigs with the test articles and challenge. Following exposure to the test articles, attempts to isolate PRRSV from serum samples were performed on MA-104 cells. Virus isolation and ELISA results were analyzed using a Chi-square analysis which tests whether the percentage of positive animals is the same in each group. White blood cell counts were performed as in Example 2.

Results and Discussion

Pigs from group 1 (vaccinated pigs) fared better in all aspects of this example than did the pigs from group 2 (pigs given sterile diluent). Clinical scores, rectal temperatures, and percent lung involvement were all higher for the pigs given sterile diluent. Weight gain and white blood cell counts were lower for the pigs receiving the sterile diluent. There was also a significant reduction in viremia beginning on day 4 post-challenge in the group given vaccine. On days 10 and 11 post-challenge, the number of animals positive for viremia decreased further in the vaccinated group, but remained the same in the group receiving sterile diluent.

An ELISA was used to monitor anti-PRRSV serological status prior to and following vaccination and challenge. All pigs were negative (S/P ratio <0.4) at the time of vaccination. All pigs including the vaccinates were negative at 7 DPV (Days Post Vaccination). Seven days later, 21 of 22 vaccinated pigs were tested as positive for antibody to PRRSV. Two pigs of group 1 remained negative during the pre-challenge period and serological converted at 8 days post challenge (8 DPC). All of the pigs in group 2 were negative at trial day 0 and remained negative throughout the pre-challenge period. On trial day 39 (8 DPC) 17 of the 22 non-vaccinated challenged pigs (Group 2) tested as sero positive. All of the pigs in group 3 (normal controls) remained sero-negative throughout the study.

Virus isolations from sera were performed before and after vaccination. Of the 22 vaccinated pigs, 17 were positive by 2 DPV, 18 were positive by 4 DPV and 19 were positive by 7 DPV. Following vaccination, vaccine virus was not recovered at all from one pig and not until 0 DPC for another. These results correspond to the sero-negative status of these pigs during the post vaccination observation period. At the time of challenge, 55% of the vaccinated pigs were viremic positive. Following challenge, this percentage rose to 82% (at 2 DPC) and gradually decreased to 9% on 11 DPC. All pigs in group 2 were negative at 0 DPC and increased to 82% positive at 2 DPC and 91% at 4 DPC. On 6 and 10 DPC, group 2 was approximately 82% virus positive and 73% of this group was positive on 11 DPC. The normal controls, group 3, remained negative for the duration of the study.

Rectal temperature monitoring showed an overall group increase experienced by group 2. One-half of the pigs in this group experienced a rise of 1° F. over the pre-challenge average for 2 or more days during the 11 day observation period. In comparison, only four of the 22 pigs in the vaccinated group experienced temperatures of 1° F. over their pre-challenge average. The average duration of those animals experiencing elevated temperatures for two or more days was 2.2 days for group 1 and 4 days for group 2. None of the pigs in group 3 experienced increases of 1° F. over their pre-challenge average for two days or longer.

Weight gain was monitored over the 11 day observation period. Pigs in group 3 gained an average of 1.06 pounds/day, pigs in group 2 gained an average of 0.94 pounds/day and pigs in group 1 gained an average of 0.53 pounds/day. Therefore, non-vaccinated challenged pigs gained only about 57% as much weight as did vaccinated challenged pigs and only 50% as much weight as the control group.

Leukopenia (white blood cell counts) were monitored during the post challenge observation period. Group 3 experienced a 5% reduction in the group average on trial day 33 (2 DPC) when compared to the pre-challenge average. For group 2, white blood cell counts dropped an average of 41% and did not return to pre-challenge levels until 11 DPC. The vaccinated group experienced a group average drop of 12% on trial day 34 (3 DPC). The counts returned to pre-challenge level on the next day and remained equal to the pre-challenge level for the duration of the observation period.

Daily clinical observations were made from trial day 28 (−4 DPC) through trial day 42 (11 DPC). All pigs were free of any observable clinical signs during the pre-challenge period. Group 3 remained free of any clinical signs for the duration of the post challenge period. Five of the pigs in group 2 were observed to have post challenge clinical signs. These signs became evident at 6 DPC and were not considered to be severe. The vaccinated pigs had only 1 clinical sign observed during the 11 day post challenge observation period.

At the termination of the study, lungs were evaluated for observable lung lesions. Group 3 had normal lungs and a group average score of 0.02. The individual pig scores for group 2 ranged from a low of 33 to a high of 98 for a group average of 78.33. The scores of the vaccinated group ranged from 30 to a high of 90 with a group average of 53.20.

The data in this example demonstrated the efficacy of a modified live Atypical PRRS viral vaccine. The vaccine was administered at a minimal dose of 2.0 logs per dose containing the fifth passage beyond the MSV (JA-142, passage 205). Efficacy of the vaccine was demonstrated by significantly reducing the extent of lung lesions, the severity of post challenge leukopenia, and post challenge fever. Additionally, a normal growth rate was maintained in vaccinated/challenged pigs compared to that achieved by the normal control pigs and significantly better than that achieved by non-vaccinated/challenged pigs.

EXAMPLE 6

Materials and Methods

This example compared four groups, groups 1, 2, and 3 having twenty pigs each, and group 4 having 10 pigs. Group 1 was inoculated intramuscularly (IM) with PRRS MSV, JA-142, passage 205, at a titer of about 2,5 logs/dose. Group 2 was inoculated intra-nasally with PRRS MSV, JA-142, passage 205, at a titer of about 5.0 logs/dose. Group 3 was inoculated IM with sterile diluent. Group 4 acted as strict controls. Pigs were challenged with a PRRSV isolate from South Dakota State University (SDSU) with an RFLP pattern of 144 on day 28 post-vaccination. Body temperatures of the pigs were monitored daily following challenge. Each animal was weighed at vaccination, challenge, weekly for the duration of the study, and necropsy. Blood samples were collected weekly following vaccination and every two days following challenge. The health status of each animal was monitored daily for the duration of the study. At the termination of the study, animals were sacrificed and their lungs scored for percent lung involvement.

PPRSV ELISA assays were performed following the exposures of the pigs with the test articles and challenge. Attempts to isolate PRRSV from serum samples were also performed on MA-104 cells following exposure to the test articles. WBC counts and clinical observations were determined post inoculation as in Example 2.

Results and Discussion

At zero days post vaccination (DPV), all pigs in this example were serologically negative to PRRSV as indicated by having a S/P ratio <0.4. At 14 DPV, 70% of the pigs in group 1 and 95% of the pigs in group 2 tested positive for the presence of anti-PRRSV antibody. Only one vaccinated pig of group 1, remained sero-negative throughout the pre-challenge period. This pig became sero-positive at seven days post challenge (DPC). All of the pigs in groups 3 and 4 remained negative throughout the pre-challenge period. At nine DPC, all of the pigs in group 3, the sterile diluent treated group, tested positive by ELISA for PRRSV antibody. The normal controls, group 4, remained negative for the duration of the study.

The virus isolation results correlated well with serological results. Only one pig remained negative for virus isolation from serum and this corresponded to the sero-negative status during the post vaccination period. These results indicate a relationship between post vaccination viremia and serological conversion with vaccine dosage. Group 2 was 100% sero-positive at 14 DPV as compared to 70% for group 1. The high dose group (group 2) was 85% and 90% viremia positive at 14 and 21 DPV, respectively. In comparison, the low dose group (group 1) was 55% and 85% positive for the same test days.

Following challenge, 89% of the animals in group 3 experienced temperatures that were one degree F or greater than the pre-challenge values for two or more days. In group 1, 75% of the animals experienced temperatures of one degree or greater for two or more days. While only 45% of the animals of group 2 experienced elevated temperatures. In comparison, 30% of the animals in the normal control group (group 4) experienced elevated temperatures for two or more days during the 11 day observation period.

Treatment with either the high vaccine dose or the low vaccine dose appeared to have no detrimental effect on the growth performance during the post-vaccination period (-3 DPV to 28 DPV). The average daily weight gain for groups 1 and 2 was 0.77 lbs./day and 0.76 lbs./day, respectively. For comparison, groups 3 and 4 had average daily weight gains of 0.77 lbs. and 0.78 lbs., respectively. Following challenge, the vaccinated groups outperformed the sterile diluent group by 0.05 lbs./day (group 1) and 0.15 lbs./day (group 2). The normal controls outgained the vaccinates during the same time period by an average of 0.4 to 0.5 lbs./day.

Eighty-four percent (16 of 19) of group 3, the sterile diluent treatment group, experienced a 25% or greater drop in their WBC count for one or more days after challenge. The normal controls had 3 of 10 (30%) that had experienced similar decreases. Following challenge, the vaccinated groups, the low dose (group1) and the high dose (group2) had 11 of 20 (55%) and 3 of 20 (15%) experiencing leukopenia of 25% for one or more days.

The clinical observations made prior to the challenge indicated that the pigs were of good health status. Following challenge, the level of health status did not significantly change for those pigs that were challenged (groups 1, 2, & 3). Lethargy, respiratory signs, and lost appetite were the clinical signs observed and these were described as mild in severity. The clinical signs reported for one pig in group 2 could be attributed to the bacterial pneumonia (see discussion below on lung lesions) that it was experiencing. The normal control group (group 4) was free of any observable clinical signs during the 11 day observation period.

At the termination of the study, pigs were sacrificed and the lungs were observed for PRRS-like lesions to score the extent of lung involvement. The percent of involvement was scored for each lobe then multiplied by the percent the lung represented for the total lung capacity. For example, 50% lung involvement for a diaphragmatic lobe was then multiplied by 25% to equal 12.5% of the total lung capacity. The maximum score that could be obtained was 100. The group average lung score for the normal controls (group 4) was zero. The group average score for the sterile diluent treatment group (group 3) was 70.08. The vaccinated treatment groups average scores were 48.83 for the low dose (group 1) and 17.76 for the high dose (group 2). One pig was observed to have a lung score of 62.5, the highest score within group 2. The lesions noted on this pig's lungs were described to be associated with bacterial pneumonia.

From the results of this study, both dosage levels of the atypical PRRS MSV vaccine reduced the severity of the clinical signs associated with the respiratory disease caused by the PRRSV. A full field dose outperformed the minimal dose as indicated by the significant reduction in lung lesion scores.

EXAMPLE 7

Materials and Methods

This example determined the sequence of the attenuated MSV, JA-142 from the 201st passage as well as the sequence of passage 3 of the field isolate virus, JA-142. The attenuated virus isolate was obtained from the master seed stock representing the 201st passage in MA-104 simian cells of a PRRSV isolated from swine affected with PRRS.

The virus was grown on 2621 cells, a monkey kidney cell line, also referred to as MA-104 and as USU-104 (Gravell et al., 181 Proc. Soc. Exp. Biol. Med. 112–119 (1986), Collins et al., Isolation of Swine Infertility and Respiratory Syndrome Virus (Isolate ATCC VR-2332) inNorth America and Experimental Reproduction of the Disease in Gnotobiotic Pigs, 4 J. Vet. Diagn. Invest. 117–126 (1992)) (the teachings of which are hereby incorporated by reference). Cells were cultured in 50 ml Dulbecco modified Eagle's MEM medium (Life Technologies, Inc., Gaithersburg, Md.), supplemented with 10% fetal calf serum and 50 $\mu$g/ml gentamicin (Sigma Chemical Co., St. Louis, Mo.) in a 5% humidified $CO_2$ atmosphere at 37° C. in 75 $cm^2$ plastic tissue culture flasks. Cells were maintained by passage at 5–7 day intervals. Cells were dislodged from the surface with trypsin-versene and split 1:4. To infect cells, media was decanted and 1 ml of cell supernatant containing virus at a titer of approximately $10^{-5-106}$ tissue culture infective doses ($TCID_{50}$) was added for 30 min. Thirty ml fresh media containing 4% fetal calf serum was added. Cells were incubated as described above for 5 days, at which time cytopathic effect was evident in the culture. Culture medium containing virus was centrifuged at 2000 rpm in a Beckman TJ6 centrifuge to pellet cellular debris.

Viral genomic RNA was purified by adding 1120 $\mu$l of prepared Buffer AVL (QIAamp Viral RNA Isolation Kit, Qiagen)(QIAGEN, Inc. Valencia, Calif.)/carrier RNA to a 280 $\mu$l sample of virus-containing culture medium. The mixture was vortexed and incubated at room temperature for 10 min. 1120 $\mu$l ethanol was added and the mixture was inverted several times. RNA was absorbed to the matrix of a QIAamp spin column by repeated centrifugation of 630 $\mu$l aliquots at 6,000×g for 1 min. The column was washed with 500 $\mu$l buffer AW and centrifuged to remove all traces of wash solution. RNA was eluted from the column with 60 $\mu$l of diethylpyrocarbonate-treated water at room temperature. Purified RNA was stored at −70° C. or used immediately for synthesis of cDNA.

For cDNA synthesis, viral RNA was heated at 67° C. for 7 min, primed with random hexamers or PRRSV-specific primers, and reverse transcribed with Superscript II RNase H-reverse transcriptase (RT) (Life Technologies, Inc.). Reactions contained 5 mM $MgCl_2$, 1×standard buffer II (Perkin Elmer Corp. Wellesley, Mass.), 1 mM each of dATP, dCTP, dGTP and dTTP, 1 unit/$\mu$l of RNase inhibitor, 2 units of RT, and 1 ×l of RNA in a 40 $\mu$l reaction. Reaction mixtures were incubated for 15 min at 42° C., for 5 min at 99° C. and for 5 min at 5° C.

Polymerase chain reaction (PCR) was performed to obtained DNA fragments for sequencing as follows: 10 µl portions of cDNA reaction mixture were combined with the following reagents, resulting in a 25 µl reaction containing 2 mM $MgCl_2$, 1×standard buffer II (Perkin Elmer), 0.2 mM each of dATP, dCTP, dGTP and dTTP, 0.3 µM of 5'- and 3'-PRRSV-specific primer, and 0.375 units AmpliTaq Taq polymerase (Perkin Elmer). Reactions were prepared by heating for 4 min at 93° C. in athermal cycler, then 35 cycles consisting of 50–59° C. for 30 sec, 72° C. for 30–60 sec, and 94° C. for 30 sec. Specific times and temperatures varied depending on the annealing temperatures of the primers in each reaction and the predicted length of the amplification product. A final incubation was performed for 10 min at 72° C. and reactions were placed at 4° C. PCR products were purified with a Microcon 100 kit (Amicon, Bedford, Mass.).

Rapid amplification of cDNA ends (RACE) PCR was performed to obtain the extreme 5'-end sequence of the genomic RNA, based on the method of Frohman, Mass., On Beyond Classic RACE (Rapid Amplification of cDNA Ends), 4 PCR Methods and Applications S40–S58 (1994) (the teachings of which are hereby incorporated by reference). Viral RNA was isolated and converted to cDNA as described above, with random hexamers as primers. Reaction products were purified on a Microcon 100 column (Amicon). A poly(dA) tail was added to the 3'-end by incubating 10 µl of cDNA in a 20 µl volume containing 1×buffer 4 (New England Biolabs, Beverly, Mass.), 2.5 mM $CoCl_2$, 0.5 mM dATP and 2 units terminal transferase (New England Biolabs), for 15 min at 37° C. The reaction was stopped by heating for 5 min at 65° C. and then was diluted to 200 µl with water.

PCR was performed using the Expanda Long Template PCR System (Boehringer Mannheim, Mannheim, Germany) in a 50 µl reaction volume containing 10 µl of diluted, poly(dA)-tailed cDNA, 1×buffer 3, 0.35 mM each of dATP, dCTP, dGTP and dTTP, 0.625 mM $MgCl_2$, 0.04 µM $Q_t$ primer (Frohman, 1994), 0.3 µM $Q_O$ primer (Frohman, 1994), 0.3 µM 5'-CGCCCTAATTGAATAGGTGAC-3' and 0.75 µl of enzyme mix. Reactions were heated at 93° C. for 2 min in a thermal cycler and cycled 25 times with each cycle consisting of 93° C. for 10 sec, 63° C. for 30 sec. and 68° C. for 12 min. After 25 cycles, the reaction was incubated at 68° C. for 7 min and held at 4° C. An aliquot of the reaction was diluted 100-fold and 5 µl of diluted product was added to a second PCR reaction containing, in 50 µl, 1×buffer 1, 0.35 mM each of dATP, dCTP, dGTP and dTTP, 0.3 µM primer Qi (Frohman, 1994), 0.3 µM 5'-CCTTCGGCAGGCGGGGAGTAGTGTTTGAGGTGCT CAGC-3', and 0.75 µl enzyme mix. Reactions were heated at 93° C. for 2 min in a thermal cycler and cycled 25 times with each cycle consisting of 93° C. for 10 sec, 63° C. for 30 sec, and 68° C. for 4 min. After 25 cycles, the reaction was incubated at 68° C. for 7 min and held at 4° C. Reaction products were electrophoresed on a 1% agarose gel and the band of approximately 1500 bp was purified using the QIAgen QXII gel purification kit. Eluted DNA was cloned into the pGEM-T vector (Promega, Madison, Wis.) using standard procedures. Individual clones were isolated and grown for isolation of plasmid DNA using QIAgen plasmid isolation kits.

PCR products and plasmid DNA were combined with appropriate primers based on related PRRSV sequences in Genbank or derived from known sequences, and subjected to automated sequencing reactions with Taq DyeDeoxy terminator cycle sequencing kits (Applied Biosystems, Foster City, Calif.) and a PR 2400 Thermocycler (Perkin Elmer) at the University of Minnesota Advanced Genetic Analysis Center. Reactions were electrophoresed on an Applied Biosystems 3700 DNA sequencer. Sequence base calling and proofreading were performed primarily with the Phred program (University of Washington Genome Center) and fragment assembly was performed primarily with the Phrap program (University of Washington Genome Center). Additional computer software including the Lasergene Package (DNASTAR Inc., Madison, Wis.), Wisconsin package version 9.1 (Genetics Computer Group, Madison, Wis.), and EuGene (Molecular Biology Information Resource, Houston, Tex.) was used to analyze the sequence. The final viral genomic sequence was assembled from approximately 100 PCR reactions and 428 DNA sequencing reactions.

Results

The results of Example 7 are given as SEQ ID Nos. 1 and 2 wherein SEQ ID No. 1 represents the sequence of the 201st passage of the Master Seed Virus, JA 142 and SEQ ID No. 2 represents the sequence of the field-isolated virulent virus, JA 142 after three passages.

We claim:

1. In a method for attenuating a virus, said virus being culturable in cell culture, said method including the steps of successively replicating said virus through inoculation and replication of the virus in respective individual cell cultures until attenuation is achieved, each of said successive inoculations occurring after cytopathic effect is observed in a previously inoculated cell culture of said respective individual cell cultures, the improvement which comprises removing virus-containing samples from at least certain of said cell cultures while the virus is replicating at a logarithmic rate and prior to induction of cytopathic effects in said certain cell cultures, and inoculating the next respective cell culture passages with said samples, wherein said logarithmic rate refers to the time period in which the virus is replicating exponentially.

2. The method of claim 1, said removing step occuring approximately 24 hours after inoculation of said cell cultures.

3. The method of claim 1, said cell culture comprising a monolayer of cells being greater than about 70% confluent.

4. The method of claim 1 further comprising the step of periodically testing said progeny virus for attenuation.

5. The method of claim 1 further comprising the steps of retaining said certain cell cultures after said removal step, and observing whether induction of cytopathic effects occurs in said retained cell cultures.

6. The method of claim 1, said inoculation comprising the smallest number of viruses which ultimately results in CPE.

7. The method of claim 1, said logarithmic rate being determinable by the portion of a one step growth curve illustrating when the virus is replicating exponentially.

8. The method of claim 1 further including the step of providing an excess of cells in order to ensure that said virus can replicate at a logarithmic rate.

9. In a method for attenuating a virus, said virus being culturable in cell culture, said method including the steps of successively replicating said virus through inoculation and replication of the virus in respective individual cell cultures until attenuation is achieved, each of said successive inoculations occurring after cytopathic effect is observed in a previously inoculated cell culture of said respective individual cell cultures, the improvement which comprises removing virus-containing samples from at least certain of said cell cultures while the virus is replicating at a logarithmic rate and prior to induction of cytopathic effects in said certain cell cultures, and inoculating the next respective cell culture passages with said samples, wherein the period in which said virus is replicating at said logarithmic rate is determinable by the portion of a one-step growth curve in which the virus is replicating exponentially.

10. The method of claim 9 further including the step of providing an excess of cells in order to ensure that said virus can replicate at a logarithmic rate.

* * * * *